(12) United States Patent
Gizdavic-Nikolaidis et al.

(10) Patent No.: US 9,992,996 B2
(45) Date of Patent: Jun. 12, 2018

(54) BIOACTIVE ANILINE COPOLYMERS

(71) Applicant: Auckland UniServices Limited, Auckland (NZ)

(72) Inventors: Marija Gizdavic-Nikolaidis, Auckland (NZ); Allan J. Easteal, Auckland (NZ); Srdjan Stepanovic, Belgrade (RS)

(*) Notice: Subject to any disclaimer, the term of this patent is extended or adjusted under 35 U.S.C. 154(b) by 0 days. days.

(21) Appl. No.: 15/142,032

(22) Filed: Apr. 29, 2016

(65) Prior Publication Data

US 2016/0235059 A1 Aug. 18, 2016

Related U.S. Application Data

(60) Division of application No. 14/713,981, filed on May 15, 2015, now abandoned, which is a continuation of application No. 13/871,164, filed on Apr. 26, 2013, now abandoned, which is a division of application No. 12/680,113, filed as application No. PCT/NZ2008/000254 on Sep. 26, 2008, now abandoned.

(30) Foreign Application Priority Data

| Sep. 28, 2007 | (NZ) | ................................. | 562092 |
| Feb. 15, 2008 | (NZ) | ................................. | 565987 |
| Jun. 6, 2008 | (NZ) | ................................. | 570475 |

(51) Int. Cl.

| A01N 37/10 | (2006.01) |
| A01N 41/04 | (2006.01) |
| C08G 75/24 | (2006.01) |
| A01N 25/34 | (2006.01) |
| A01N 33/06 | (2006.01) |
| A01N 35/10 | (2006.01) |
| C08G 73/02 | (2006.01) |
| C09D 5/14 | (2006.01) |
| C08L 79/02 | (2006.01) |
| C09D 179/02 | (2006.01) |

(52) U.S. Cl.
CPC ............. *A01N 37/10* (2013.01); *A01N 25/34* (2013.01); *A01N 33/06* (2013.01); *A01N 35/10* (2013.01); *A01N 41/04* (2013.01); *C08G 73/0266* (2013.01); *C08G 75/24* (2013.01); *C08L 79/02* (2013.01); *C09D 5/14* (2013.01); *C09D 179/02* (2013.01)

(58) Field of Classification Search
CPC ........ A01N 33/06; A01N 35/10; A01N 41/04; A01N 25/34; A01N 37/10; C08G 73/0266; C08G 75/24; C08L 79/02; C09D 5/14; C09D 179/02
See application file for complete search history.

(56) References Cited

U.S. PATENT DOCUMENTS 6,641,755 B2 * 11/2003 Tomoike ............... H01L 27/322
252/301.35

OTHER PUBLICATIONS

Rivas et al. ("Poly(2-) and (3-aminobenzoic acids) and Their Copolymers with Aniline: Synthesis, Characterization, and Properties" in Journal of Applied Polymer Science, vol. 89, pp. 2641-2648 (2003)).*
Stejskal et al. ("Polyaniline. Preparation of a Conducting Polymer (IUPAC Technical Report)" in Pure Appl. Chem., vol. 74, No. 5, pp. 857-867, 2002.*
Nguyen et al. ("Water-Soluble Poly(aniline-co-o-anthranilic acid) Copolymers" in Macromolecules 1995, vol. 28, pp. 3411-3415.*
Mannino et al. ("Electrochemical Methods for Food and Drink Analysis" in Electroanalysis, 4 (1992), 835-840).*
Lu et al. ("Self-assembly of Poly(aniline-co-anthranilic acid) Copolymers and PVP into Fibers and Other Microstructures" in Chemistry Letters, vol. 33, No. 5 (2004).*

(Continued)

*Primary Examiner* — Blessing M Fubara
(74) *Attorney, Agent, or Firm* — Michael R. Rutherford

(57) ABSTRACT

Aniline copolymers and the synthesis thereof for use as antimicrobial (antibacterial, antifungal or antiviral material) material of for the manufacture of antimicrobial objects, suitable for use in the health, food, packaging, water, paint, wood, textile, poultry, glass, paper, rubber, ceramic, seafood, sports, plastic and agricultural industries. The copolymer may be for example (A): where for example $R^3=H_5—CO_2H$, $—CO_2Me$, or $—CO_2Et$. R is typically H or a $C_1$-$C_6$ alkyl, x is an integer between 1 and 0 and m indicates the degree of polymerization. Preferred copolymers are copolymers of aniline with 3-aminobenzoic acid, 2-aminobenzoic acid and ethyl 3-aminobenzoate.

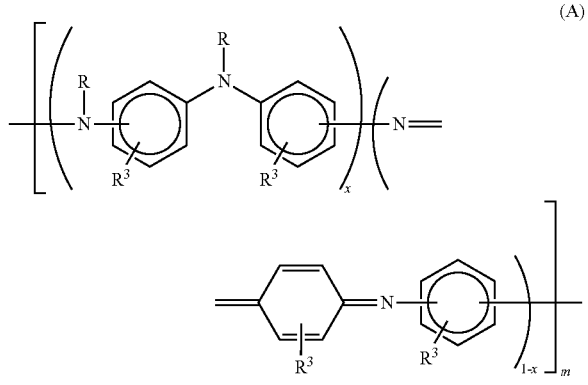

15 Claims, 15 Drawing Sheets

(56) References Cited

OTHER PUBLICATIONS

Marija R. Gizdavic-Nikolaidis, Zoran D. Zujovic, Sudip Ray, Allan J. Easteal, Graham A. Bowmaker, Chemical Synthesis and Characterization of Poly(aniline-co-ethyl 3-aminobenzoate) Copolymers, Journal of Polymer Science: Part A: Polymer Chemistry, (2010), 1339-1347, vol. 48.

* cited by examiner

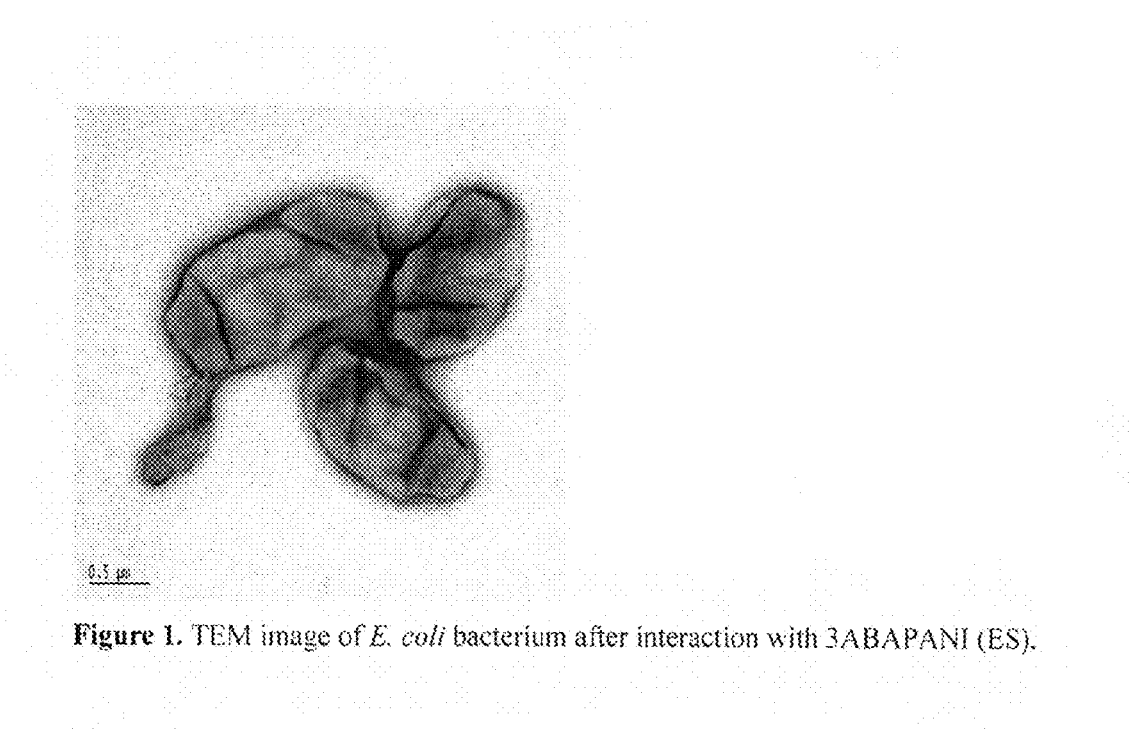
Figure 1. TEM image of *E. coli* bacterium after interaction with 3ABAPANI (ES).

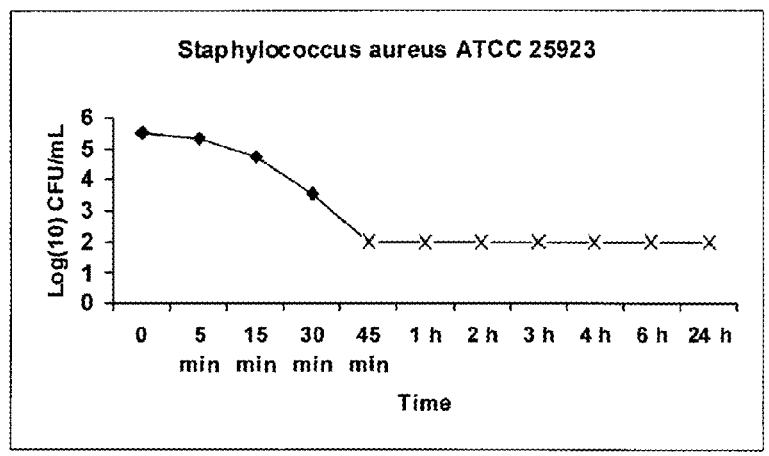
Figure 2. Log10 reduction of the viable count of *Staphylococcus aureus* ATCC 25923 in the presence of 2% 3ABAPANI (ES).

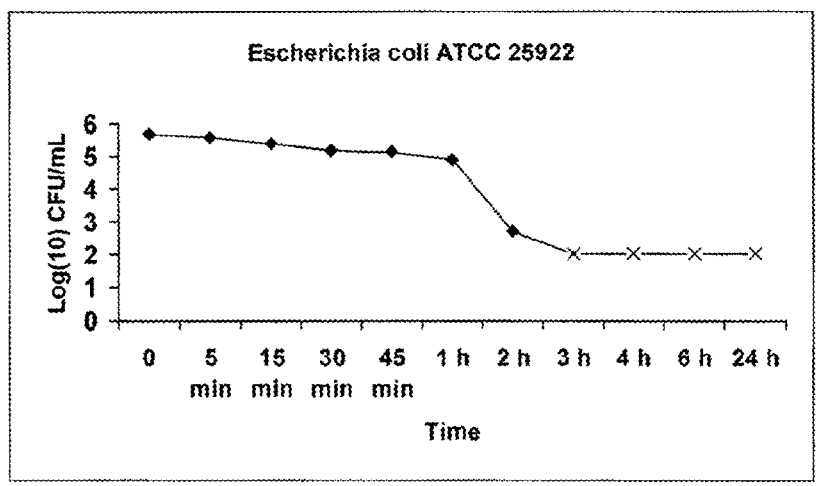
Figure 3. Log10 reduction of the viable count of *Escherichia coli* ATCC 25922 in the presence of 2% 3ABAPANI (ES).

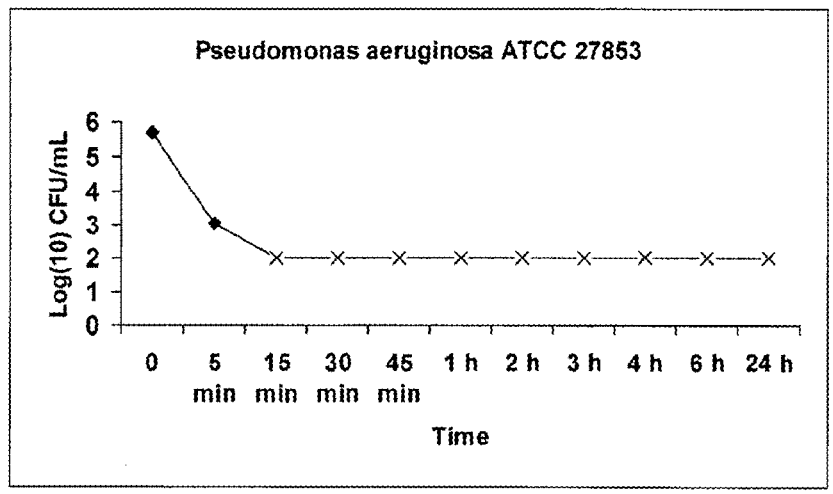
Figure 4. Log10 reduction of the viable count of *Pseudomonas aeruginosa* ATCC 27853 in the presence of 2% 3ABA PANI (ES).

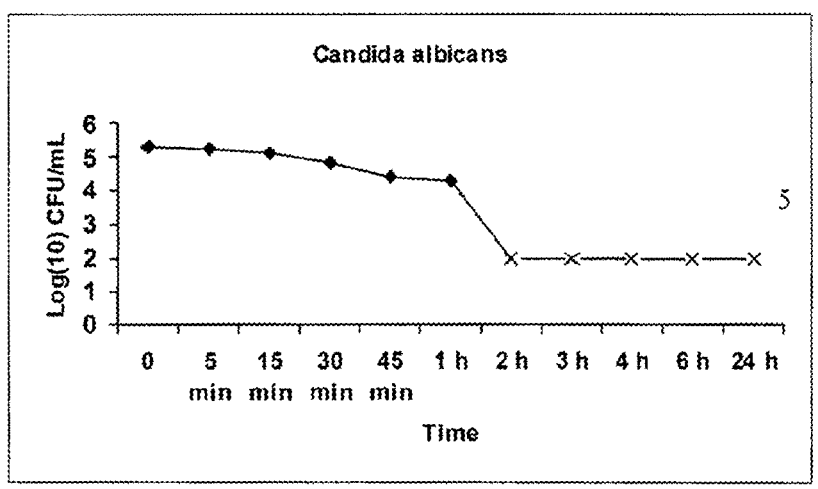
Figure 5. Log10 reduction of the viable count of *Candida albicans* in the presence of 2% 3ABAPANI (ES).

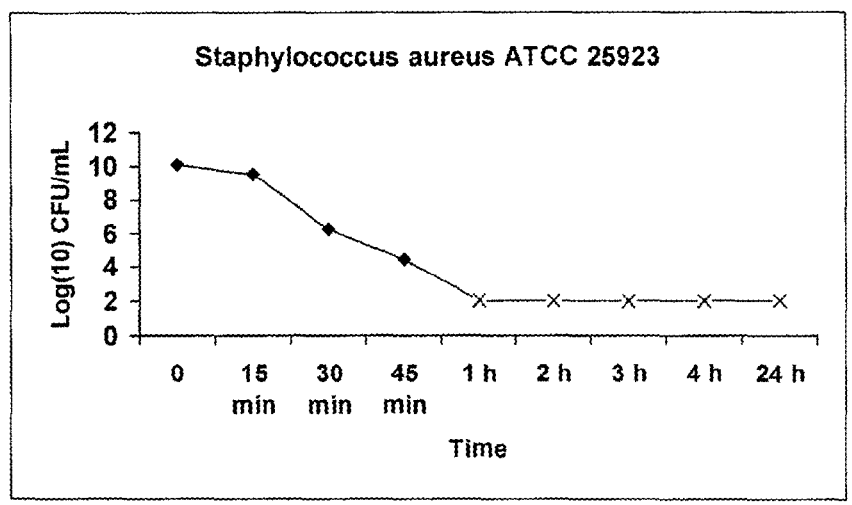
Figure 6. Log10 reduction of the viable count of *Staphylococcus aureus* ATCC 25923 in the presence of 2% 3ABAPANI (ES) - high initial inoculum.

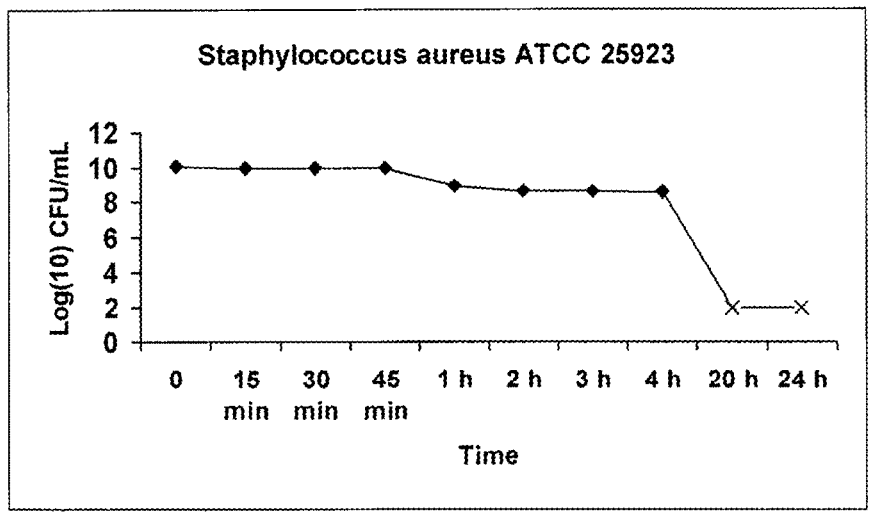
Figure 7. Log10 reduction of the viable count of *Staphylococcus aureus* ATCC 25923 in the presence of 2% 3ABAPANI (ES) and 20% plasma.

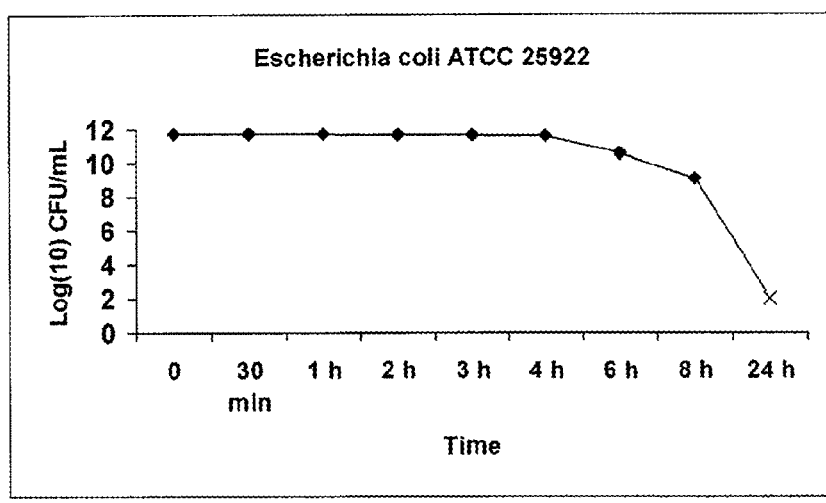
Figure 8. Log10 reduction of the viable count of *Escherichia coli* ATCC 25922 in the presence of 2% 3ABAPANI (ES) and 20% plasma.

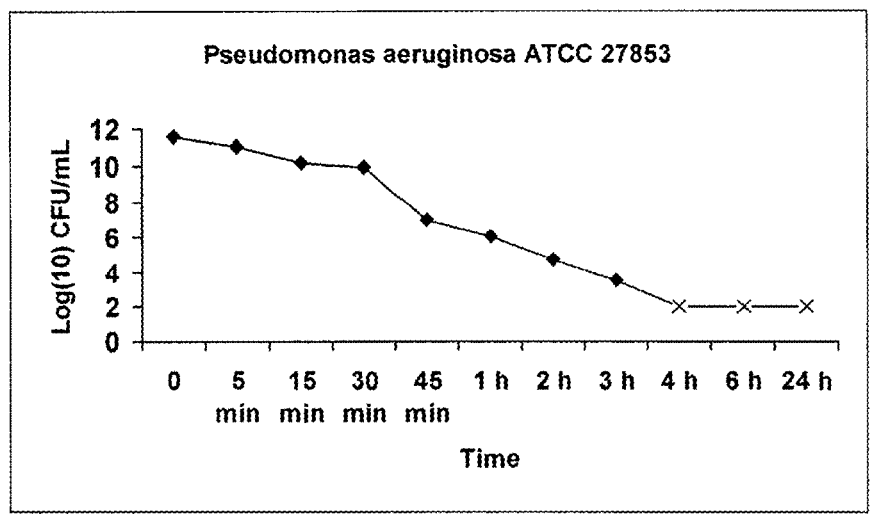
Figure 9. Log10 reduction of the viable count of *Pseudomonas aeruginosa* ATCC 27853 in the presence of 2% 3ABAPANI (ES) and 20% plasma.

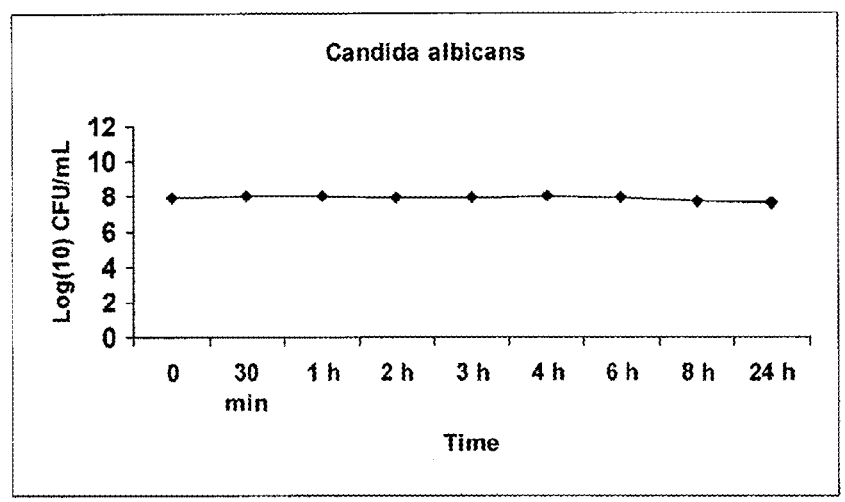
Figure 10. Log10 reduction of the viable count of *Candida albicans* in the presence of 2% 3ABAPANI (ES) and 20% plasma.

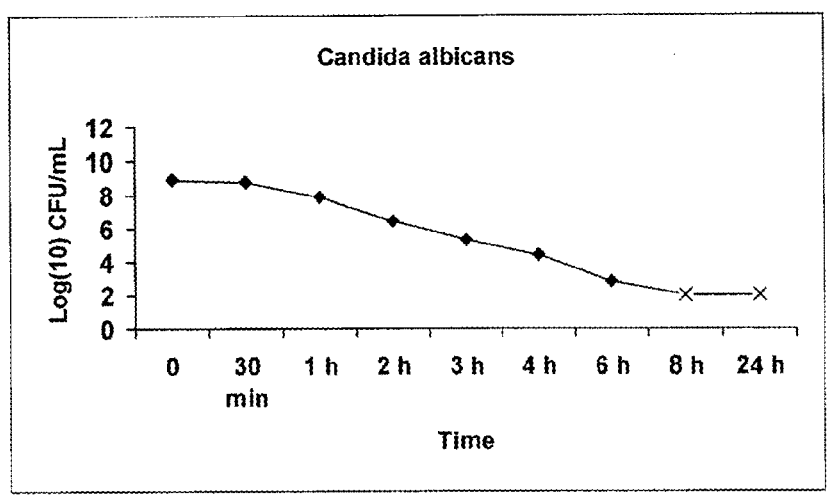
Figure 11. Log10 reduction of the viable count of *Candida albicans* in the presence of 2% 3ABAPANI (ES) and 5% plasma.

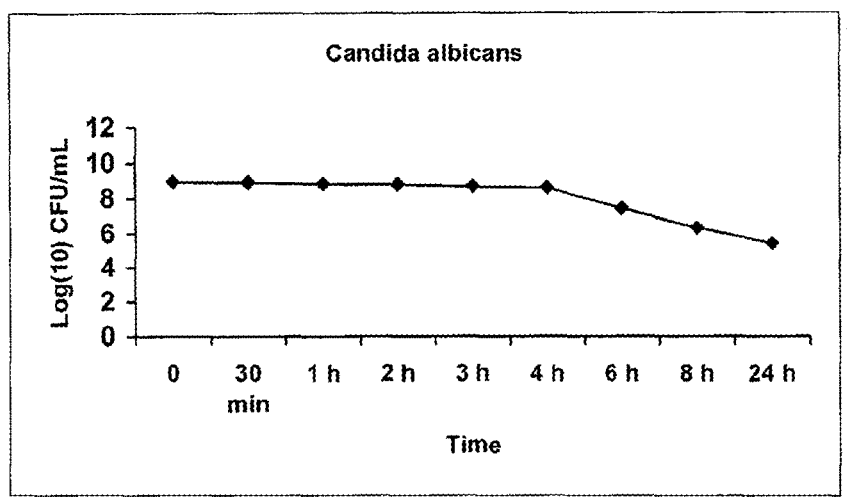
Figure 12. Log10 reduction of the viable count of *Candida albicans* in the presence of 2% 3ABAPANI (ES) and 10% plasma.

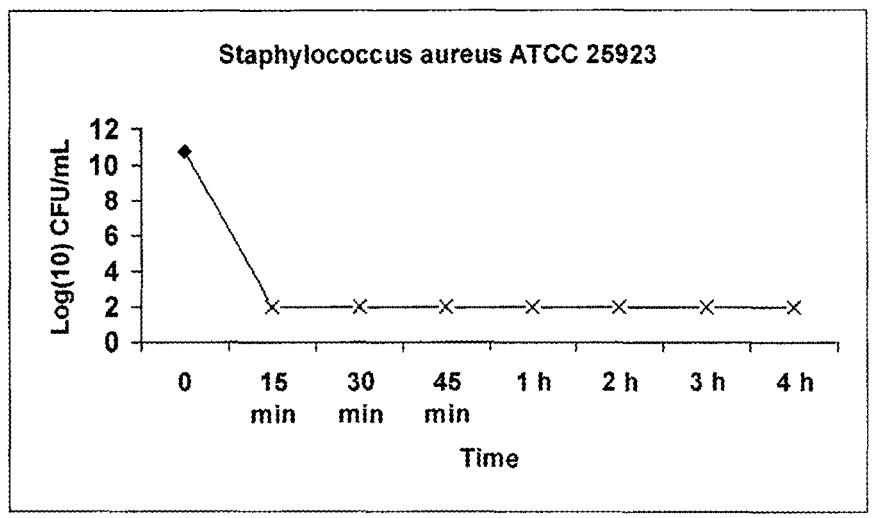
Figure 13. Log10 reduction of the viable count of *Staphylococcus aureus* ATCC 25923 in the presence of 2% 3ABAPANI (ES) and 16 mmol NAC.

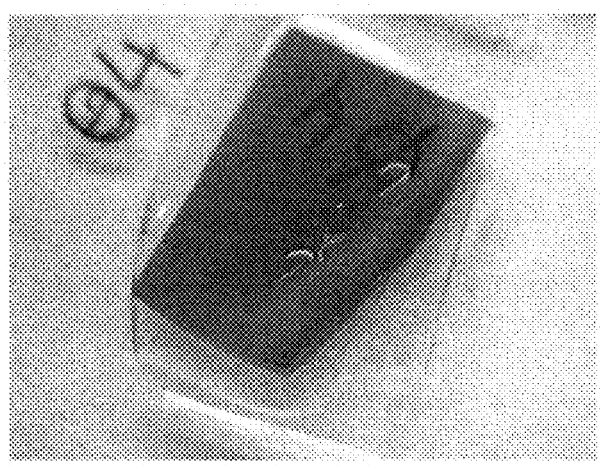
Figure 14. Film 04 (PVA and PANI) coated on PMMA after interaction with *Staphylococcus aureus* ATCC 25923.

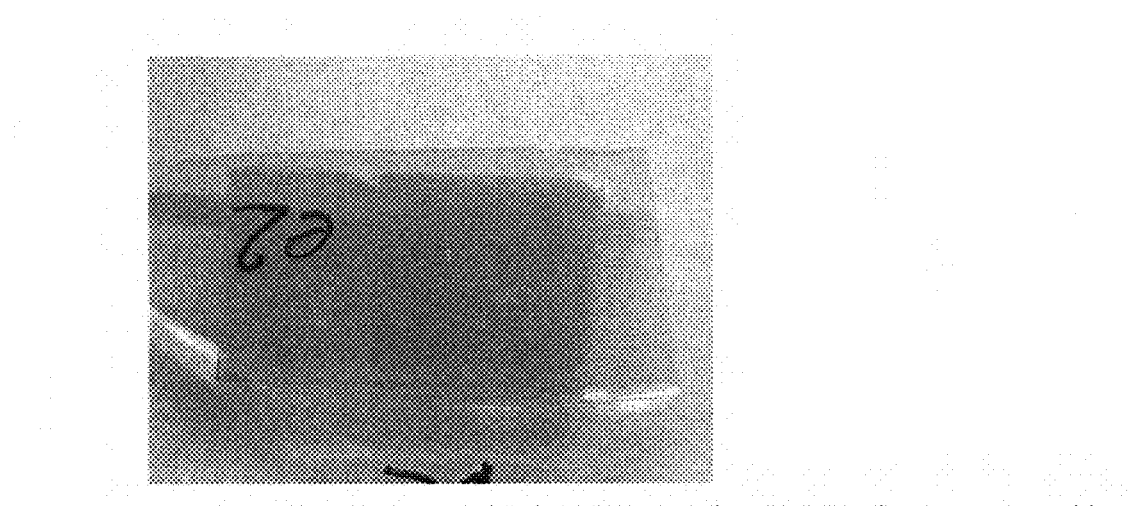
Figure 15. Film ρ2 (PVA and Poly3ABA) coated on PMMA after interaction with *Staphylococcus aureus* ATCC 25923.

BIOACTIVE ANILINE COPOLYMERS

CROSS REFERENCE TO RELATED APPLICATIONS

The present application is a Divisional Application of U.S. patent application Ser. No. 14/713,981 filed on May 15, 2015, pending, which is a continuation of Ser. No. 13/871, 164, filed Apr. 26, 2013, abandoned, which is a Divisional Application of Ser. No. 12/680,113, filed Mar. 25, 2010, abandoned, which was a National Stage Entry of International Application number PCT/NZ2008/000254 filed on Sep. 26, 2008 which designated the United States and claims benefit to New Zealand Patent application number 562092, filed on Sep. 28, 2007; New Zealand Patent Application No. 565987, filed Feb. 15, 2008; and New Zealand Patent Application No. 570475, filed Jun. 6, 2008. The entire contents of the aforementioned applications are incorporated by reference herein.

FIELD OF THE INVENTION

The present invention relates to polyaniline copolymers and the use of polyaniline copolymers as antimicrobial agents and more particularly as antibacterial, antifungal and antiviral agents.

The invention has been developed primarily for preventing bacterial and/or fungal and/or virus growth on a surface and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

The general structure of polyanilines (PANIs) is known. However, up until now, polyanilines have not been widely exploited in technological applications due to the poor processability of polyaniline, which is largely a function of its low solubility in common solvents and its poor miscibility with other polymers (H. Salavagione et al., Journal of Polymer Science: Part A: Polymer Chemistry, Vol. 42, 5587-5599 (2004)). PANI dissolves to a significant extent in only a small number of solvents eg. N-methyl-2 pyrrolidone (NMP) or hexafluoro-2-propanol (HFP). The use of HFP also has significant cost disadvantages due to its relative expense.

Films containing PANI have recently been found to act as antibacterial materials. In Chinese patent publication CN 1844245 PANI, either as a powder or in a composite film with polyvinyl alcohol or polyethylene, is disclosed as having antibacterial activity against the growth of *Escherichia coli* and staphylococcal organisms. The films contained low quantities (1-10 wt %) of PANI relative to the amount of polyvinyl alcohol or polyethylene used, which is indicative of the processability problems that would prohibit higher amounts of PANI being used.

It is an object of the present invention to overcome or ameliorate at least one of the disadvantages of the prior art, or to provide a useful alternative. More particularly, it is an object of the invention in its preferred form to provide a polyaniline polymer or copolymer which has good processability and has antimicrobial activities, in particular antibacterial and/or antifungal and/or antiviral activities.

SUMMARY OF THE INVENTION

It has been discovered by the present inventors that 5 copolymers of aniline with substituted anilines have a fast inhibitory effect on microorganisms, including pathogenic bacteria, when present in small amounts, for instance from 0.03-1 wt % upwards. The copolymers are surprisingly amenable to processing, and may for example be readily incorporated into films or gels, or electrospun as nanofibres. The terms "microorganism" "microbial" and the like as used herein is used in a broad sense and includes not only bacteria, but also fungi and viruses. Similarly, "antimicrobial" and the like is used to indicate a reduction or growth suppression in bacteria, fungi, viruses and so on.

According to a first aspect, the invention provides the use of an aniline copolymer as an antimicrobial material. Preferably, the use of the aniline copolymer is as an antibacterial and/or antifungal and/or antiviral material.

According to a second aspect, the invention provides the use of an aniline copolymer for the manufacture of an antimicrobial material. Preferably, the aniline copolymer is used for the manufacture of an antibacterial and/or antifungal and/or antiviral object.

Preferably said aniline polymer is an aniline conducting copolymer. Preferably said aniline copolymer is an antioxidant.

Preferably said aniline copolymer is soluble to at least 0.05 mg/mL in a solvent selected from the group consisting of N-methyl-2-pyrrolidone, pyridine, 2,6-dimethyl pyridine, 2,4,6-trimethyl pyridine, dimethyl sulfoxide, N,N-dimethyl acetamide anhydrous, tetrahydrofuran, dimethylformamide, hexafluoro-2-propanol, chloroform and dichloromethane.

Preferably the copolymer has a leucoemeraldine, emeraldine, or pernigraniline structure. Most preferably the copolymer has an emeraldine structure. Preferably the copolymer is in a salt or free-base form. The emeraldine salt form is the most preferred.

Preferably said copolymer is formed by reaction of aniline with a compound of formula (I)

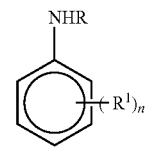

I wherein R is hydrogen or a $C_1$-$C_6$ alkyl,
n=1, 2 or 3
$R^1$ is independently selected from the group consisting of:
$C_1$-$C_6$ alkyl,
$C_1$-$C_6$ alkoxyl,
halo,
—$CO_2R^2$,
—$SO_3R^2$,
—$PO_3HR^2$,
—$COR^4$,
—$CH_2COOR^4$,
—CN,
—$CH_2OH$,
—$CH_2NH_2$,
—$CH_2CN$,
—OH, —$SO_2NH_2$, $R^2$ is selected from hydrogen, $C_1$-$C_6$ alkyl, an alkali metal, ammonium and a substituted ammonium salt; $R^4$ is selected from hydrogen, $C_1$-$C_6$ alkyl, phenyl; and salts thereof.

The benzene ring may optionally contain one or more hetero atoms in place of a carbon atom, preferably selected from N, O, S, and more preferably one, two or three nitrogen atoms.

In cases where two $R^1$ groups are present, they may be taken together to form a ring, for example if n=2 and both $R^1$ groups are COOH, then the compound may be a phthalic anhydride.

Preferably R is hydrogen and $R^1$ is, $CO_2R^2$, more preferably R is hydrogen and $R^1$ is, $CO_2H$, $CO_2Me$, or, $CO_2Et$. Most preferably formula (I) is a compound selected from the group consisting of 3-aminobenzoic acid, 2-aminobenzoic acid and ethyl 3-aminobenzoate.

When the compound of formula I has n=2, the independently variable $R^1$ groups are preferably, but not necessarily, meta to the NHR group. When the compound of formula I has n=3, the independently variable $R_1$ groups are preferably, but not necessarily, ortho and para to the NHR group.

Alternatively the copolymer may be formed by the reaction of aniline with compounds in which the aromatic ring is not necessarily benzenoid, but is any suitable aromatic ring, ie a heterocyclic ring having any number of atoms, more usually 5 or 6. That is, preferably said copolymer is formed by reaction of aniline with a compound of formula Ia,

where R, $R^1$ and n are as above, with Ar being a N-containing heterocycle such as pyridine, pyridazine, pyrimidine, pyrazine, pyrrole, pyrazole, an O-containing heterocycle such as pyran or furan, an S-containing heterocycle such as thiophen, mixed heterocyclic systems such as isoxazole or polycyclic systems such as naphthalene, quinoline or quinoxaline.

The compounds will be further described with reference to a benzene ring bearing a single $R^1$ but it will be appreciated that they will disclose compounds with any suitable aromatic ring substituted with a mixture of $R^1$ groups, or a mixture of any or all of mono, di, tri or otherwise $R^1$ substituted rings.

Other preferred comonomers include one or more compounds from the group consisting of: 3-acetylaniline; 2-aminobenzaldehyde; 2-aminobenzenesfonamide; 2-aminophenol; 3-aminophenol; 2-aminophenylacetic acid; 3-aminophenylacetic acid; 2-aminobenzonitrile; 3-aminobenzonitrile; 2-aminobenzophenone; 3-aminobenzophenone; 2-aminobenzyl alcohol; 3-aminobenzyl alcohol; 2-aminobenzylamine; 2-aminobenzyl cyanide; 2-amino-4-bromobenzoic acid; 2-amino-6-chlorobenzoic acid; 2-amino-4-chlorobenzoic acid; 2-amino-4-chlorophenol; 2-amino-4-methylphenol; 2-amino-4,6-dihydroxypyrimidine; 2-amino-1,3-diethylbenzene; 1-amino-3,5-dimethylbenzene; 2-amino-4,6-dimethylpyridine; 2-amino-4-hydroxy-6-methylpyrimidine; 5-aminoisophthalic acid; 3-amino-2-methylbenzoic acid; 2-amino-3-methylphenol; 2-amino-6-methylpyridine; 2-amino-3-picoline; 2-aminopyridine; and 3-aminopyridine.

Preferably said antimicrobial material is effective against bacteria selected from Gram-positive bacteria and Gram-negative bacteria.

Preferably said Gram-positive bacteria and said Gram-negative bacteria belong to genera selected from the group consisting of *Bordetella, Neisseria, Legionella, Pseudomonas, Salmonella, Shigella, Erwinia, Enterobacter, Escherichia, Vibrio, Haemophilus, Actinobacillus, Klebsiella, Staphylococcus, Streptococcus, Enterococcus, Corynebacterium, Listeria, Bacillus, Mycobacterium, Enterococcus, Leptospira, Serpulina, Mycoplasma, Bacteroides, Yersinia, Chlamydia, Porphyromonas, Pasteurella, Peptostreptococcus, Propionibacterium, Dermatophilus, Campylobacter* and *Erysipelothrix.*

Even more preferably, said Gram-positive bacteria and said Gram-negative bacteria are selected from the group consisting of *Staphylococcus aureus, Escherichia coli, Pseudomonas aeruginosa, Salmonella enterica serotype Enteritidis, Enterococcus* sp., *Staphylococcus sciuri, Enterobacter* sp., and *Campylobacter jejuni.*

Preferably said antimicrobial material is effective against fungal genera selected from the group consisting of *Aspergillus, Blastomyces, Candida, Coccidioides, Cryptococcus, Epidermophyton, Histoplasma, Microsporum, Mucor, Rhizopus, Sporothrix, Trichophyton, Paracoccidioides, Absidia, Fusarium, Penicillium, Torulopsis, Trichosporon, Rhodotorula, Malassezia, Cladosporium, Fonsecea* and *Phialophora.*

The viruses may be DNA viruses or RNA viruses. Preferably said DNA viruses and said RNA viruses belong to families selected from the group consisting of Parvoviridae, Papillomaviridae, Polyomaviridae, Adenoviridae, Hepadnaviridae, Herpesviridae, Poxviridae, Picornaviridae, Caliciviridae, Reoviridae, Togaviridae, Flaviviridae, Coronaviridae, Orthomyxoviridae, Paramyxoviridae, Rhabdoviridae, Filoviridae, Bunyaviridae, Arenaviridae and Retroviridae.

Preferably said object is employed in the health industry, food industry, packaging industry, textile industry, plastic industry, glass industry, paper industry, rubber industry, ceramic industry, water industry, paint industry, wood industry, poultry industry, seafood industry, sports industry and agricultural industry.

The materials of the present invention can be used to fabricate objects suitable for use in a wide range of applications requiring combating of microbes, provided the physical properties of the material are suitable. Some preferred but non-limiting examples of antimicrobial objects include medical dressings, urine catheters, endoscopes, medical instruments, hospital furniture, pipettes, masks, gloves, floors, doors and walls, food utensils and food packets, food processing surfaces and apparatus, plastic film wraps and plastic containers, computer keyboards and mouses, cosmetics, handles, water tanks, membranes for water purification, toilets, door handles, drainage pipes, water pipes, ear pieces, shoe insoles, pools, bags for urine or feces or blood platelets, air-conditioning units, filtration equipment, pasteurization equipment and furniture.

In one particularly preferred embodiment, the aniline copolymers of the present invention are incorporated into films or wraps or nanofibres which are useful in the food storage and food packaging industry or which may be useful as wound dressings or for bandages. The aniline copolymers may be present in non-antimicrobial and non-metallic films, gels, wraps or dressings either as a component which is dispersed, blended or alloyed with the other film, gel, wrap or dressing forming components, or the aniline copolymers may be present in a form covalently bonded with the other film, gel, wrap or dressing forming components.

According to a third aspect, the invention provides an aniline copolymer of the following formula:

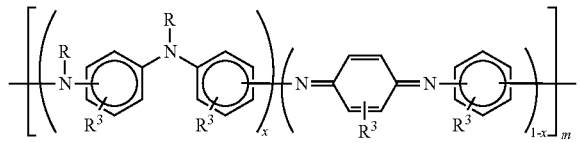

where $R^3$=H or $R^1$ as above, R is as above, x is an integer between 1 and 0 and m indicates the degree of polymerisation. Preferably, the compound is not polyaniline per se.

The benzene rings may optionally contain one or more hetero atoms in place of a carbon atom, preferably selected from N, O, S, and more preferably one, two or three nitrogen atoms.

The degree of polymerisation, m, can be anywhere from 1 up to $10^8$.

According to a fourth aspect, the invention provides a process for preparing an aniline copolymer, said process comprising the step of reacting aniline with a compound of formula (I) in a mineral acid solution containing an oxidizing agent

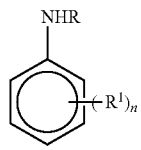

I wherein R is hydrogen or a $C_1$-$C_6$ alkyl,
n=1, 2 or 3
$R^1$ is independently selected from the group consisting of:
$C_1$-$C_6$ alkyl,
$C_1$-$C_6$ alkoxyl,
halo,
—$CO_2R^2$,
—$SO_3R^2$,
—$PO_3HR^2$,
—$COR^4$,
—$CH_2COOR^4$,
—CN,
—$CH_2OH$,
—$CH_2NH_2$,
—$CH_2CN$,
—OH,
—$SO_2NH_2$, $R^2$ is selected from hydrogen, $C_1$-$C_6$ alkyl, an alkali metal, ammonium and a substituted ammonium salt;
$R^4$ is selected from hydrogen, $C_1$-$C_6$ alkyl, phenyl; and salts thereof.

The benzene ring may optionally contain one or more hetero atoms in place of a carbon atom, preferably selected from N, O, S, and more preferably one, two or three nitrogen atoms.

In cases where two $R^1$ groups are present, they may be taken together to form a ring, for example if n=2 and both $R^1$ groups are COOH, then the compound may be a phthalic anhydride.

Preferably R is hydrogen and $R^1$ is, $CO_2R^2$, more preferably R is hydrogen and $R^1$ is, $CO_2H$, $CO_2Me$, or, $CO_2Et$.

Most preferably formula (I) is a compound selected from the group consisting of 3-aminobenzoic acid, 2-aminobenzoic acid and ethyl 3-aminobenzoate.

When the compound of formula I has n=2, the independently variable $R^1$ groups are preferably, but not necessarily, meta to the NHR group. When the compound of formula I has n=3, the independently variable $R_1$ groups are preferably, but not necessarily, ortho and para to the NHR group.

Alternatively the copolymer may also be formed by the reaction of aniline with compounds in which the aromatic ring is not be benzenoid, but is any suitable aromatic ring, ie a heterocyclic ring having any number of atoms, more usually 5 or 6. That is, preferably said copolymer is formed by reaction of aniline with a compound of formula Ia,

Ia where R, $R^1$ and n are as above, with Ar being a N-containing heterocycle such as pyridine, pyridazine, pyrimidine, pyrazine, pyrrole, pyrazole, an O-containing heterocycle such as pyran or furan, an S-containing heterocycle such as thiophen, mixed heterocyclic systems such as isoxazole or polycyclic systems such as naphthalene, quinoline or quinoxaline.

The compounds will be further with reference to a benzene ring bearing a single $R^1$ but it will be appreciated that they will encompass compounds further substituted with having a mixture of $R^1$ groups, or a mixture of any or all of mono, di, tri or otherwise $R^1$ substituted rings.

Other preferred comonomers include one or more compounds from the group consisting of: 3-acetylaniline; 2-aminobenzaldehyde; 2-aminobenzenesfonamide; 2-aminophenol; 3-aminophenol; 2-aminophenylacetic acid; 3-aminophenylacetic acid; 2-aminobenzonitrile; 3-aminobenzonitrile; 2-aminobenzophenone; 3-aminobenzophenone; 2-aminobenzyl alcohol; 3-aminobenzyl alcohol; 2-aminobenzylamine; 2-aminobenzyl cyanide; 2-amino-4-bromobenzoic acid; 2-amino-6-chlorobenzoic acid; 2-amino-4-chlorobenzoic acid; 2-amino-4-chlorophenol; 2-amino-4-methylphenol; 2-amino-4,6-dihydroxypyrimidine; 2-amino-1,3-diethylbenzene; 1-amino-3,5-dimethylbenzene; 2-amino-4,6-dimethylpyridine; 2-amino-4-hydroxy-6-methylpyrimidine; 5-aminoisophthalic acid; 3-amino-2-methylbenzoic acid; 2-amino-3-methylphenol; 2-amino-6-methylpyridine; 2-amino-3-picoline; 2-aminopyridine; and 3-aminopyridine.

Any suitable oxidising agent may be used. Preferably the oxidising agent is selected from the group consisting of ammonium persulphate, potassium ferricyanide, an iodate salt and hydrogen peroxide. Most preferably, the oxidising agent is potassium iodate. For preference, suitable mineral acids are hydrochloric, sulphuric, nitric and perchloric acids. Most preferably the mineral acid is hydrochloric acid. Preferably the iodate salt is potassium iodate and the mineral acid is hydrochloric acid.

Preferably the ratio of said aniline to said compound of formula (I) is 1:2 to 2:1, and more preferably said ratio is about 1:1.

The aniline copolymer is also preferably purified by treatment with a compound in which the aniline copolymer is largely insoluble, but which acts as a solvent for the removal of starting monomers, intermediate oligomers and the like. Acetone is a preferred compound for this purpose.

The invention also provides an aniline copolymer when prepared by the process of the preceding aspect.

According to a fifth aspect, the invention provides an aniline copolymer wherein said copolymer is produced by reacting aniline and a compound of formula (I)

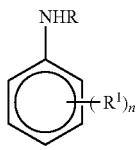

wherein R is hydrogen or a $C_1$-$C_6$ alkyl,
n=1, 2 or 3
$R^1$ is independently selected from the group consisting of:
$C_1$-$C_6$ alkyl,
$C_1$-$C_6$ alkoxyl,
halo,
—$CO_2R^2$,
—$SO_3R^2$,
—$PO_3HR^2$,
—$COR^4$,
—$CH_2COOR^4$,
—CN,
—$CH_2OH$,
—$CH_2NH_2$,
—$CH_2CN$,
—OH,
—$SO_2NH_2$, $R^2$ is selected from hydrogen, $C_1$-$C_6$ alkyl, an alkali metal, ammonium and a substituted ammonium salt; $R^4$ is selected from hydrogen, $C_1$-$C_6$ alkyl, phenyl; and salts thereof.

The benzene ring may optionally contain one or more hetero atoms in place of a carbon atom, preferably selected from N, O, S, and more preferably one, two or three nitrogen atoms.

In cases where two $R^1$ groups are present, they may be taken together to form a ring, for example if n=2 and both $R^1$ groups are COOH, then the compound may be a phthalic anhydride.

Preferably R is hydrogen and $R^1$ is, $CO_2R^2$, more preferably R is hydrogen and $R^1$ is, $CO_2H$, $CO_2Me$, or, $CO_2Et$. Most preferably formula (I) is a compound selected from the group consisting of 3-aminobenzoic acid, 2-aminobenzoic acid and ethyl 3-aminobenzoate.

When the compound of formula I has n=2, the independently variable $R^1$ groups are preferably, but not necessarily, meta to the NHR group. When the compound of formula I has n=3, the independently variable $R^1$ groups are preferably, but not necessarily, ortho and para to the NHR group.

The copolymer may also be formed by the reaction of aniline with compounds in which the aromatic ring is not be benzenoid, but is any suitable aromatic ring, ie a heterocyclic ring having any number of atoms, more usually 5 or 6. That is, preferably said copolymer is formed by reaction of aniline with a compound of formula Ia,

where R, $R^1$ and n are as above, with Ar being a N-containing heterocycle such as pyridine, pyridazine, pyrimidine, pyrazine, pyrrole, pyrazole, an O-containing heterocycle such as pyran or furan, an S-containing heterocycle such as thiophen, mixed heterocyclic systems such as isoxazole or polycyclic systems such as naphthalene, quinoline or quinoxaline.

The compounds will be further with reference to a benzene ring bearing a single $R^1$ but it will be appreciated that they will encompass compounds further substituted with having a mixture of $R^1$ groups, or a mixture of any or all of mono, di, tri or otherwise $R^1$ substituted rings.

Other preferred comonomers include one or more compounds from the group consisting of: 3-acetylaniline; 2-aminobenzaldehyde; 2-aminobenzenesfonamide; 2-aminophenol; 3-aminophenol; 2-aminophenylacetic acid; 3-aminophenylacetic acid; 2-aminobenzonitrile; 3-aminobenzonitrile; 2-aminobenzophenone; 3-aminobenzophenone; 2-aminobenzyl alcohol; 3-aminobenzyl alcohol; 2-aminobenzylamine; 2-aminobenzyl cyanide; 2-amino-4-bromobenzoic acid; 2-amino-6-chlorobenzoic acid; 2-amino-4-chlorobenzoic acid; 2-amino-4-chlorophenol; 2-amino-4-methylphenol; 2-amino-4,6-dihydroxypyrimidine; 2-amino-1,3-diethylbenzene; 1-amino-3,5-dimethylbenzene; 2-amino-4,6-dimethylpyridine; 2-amino-4-hydroxy-6-methylpyrimidine; 5-aminoisophthalic acid; 3-amino-2-methylbenzoic acid; 2-amino-3-methylphenol; 2-amino-6-methylpyridine; 2-amino-3-picoline; 2-aminopyridine; and 3-aminopyridine.

The aniline copolymer is also preferably purified by treatment with a compound in which the aniline copolymer is largely insoluble, but which acts as a solvent for the removal of starting monomers, intermediate oligomers and the like. Acetone is a preferred compound for this purpose.

According to a sixth aspect, the invention provides an antimicrobial object including an aniline copolymer.

According to a seventh aspect, the invention provides a product incorporating an aniline copolymer. The product may be, for preference, a film suitable for use in food packaging. Alternatively, the product may be, for preference, a wound dressing.

According to an eighth aspect the invention provides a composite material comprising an aniline copolymer, preferably those of the present invention, and at least one other substance. The composite material may be in the form of a powder, a blend or as a coating on the at least one other substance.

For preference, the at least one other substance is selected from the group consisting of poly(vinyl alcohol), poly(vinyl acetate), poly(methyl methacrylate) or acrylic polymers, poly(ethylene terephthalate) or other polyesters, polyamides, polyethylene and polypropylene, polyvinylidene fluoride, ethylene vinyl acetate copolymers, methyl acrylate copolymers, butane copolymers, hexane copolymers, rubber, natural rubber latex, acrylic latexes, epoxy latexes, ethyl cellulose, cellulose, polysaccharides, and proteins.

The composite material is preferably synthesised by in situ polymerization, surface coating, extrusion, co-extrusion, or blow molding.

Preferably, the composite material has aniline copolymer present in a MIC such that the composite has suitable antimicrobial activity.

The invention also provides a method of preserving food comprising the step of contacting the food with an aniline copolymer.

DESCRIPTION OF THE DRAWINGS

FIG. 1 shows a TEM image of *E. coli* bacteria after interaction with 3ABAPANI (ES).

FIG. 2 shows a graph of Log 10 reduction of the viable count of *Staphylococcus aureus* ATCC 25923 in the presence of 2% 3ABAPANI (ES).

FIG. 3 shows a graph of Log 10 reduction of the viable count of *Escherichia coli* ATCC 25922 in the presence of 2% 3ABAPANI (ES).

FIG. 4 shows a graph of Log 10 reduction of the viable count of *Pseudomonas aeruginosa* ATCC 27853 in the presence of 2% 3ABA PANI (ES).

FIG. 5 shows a graph of Log 10 reduction of the viable count of *Candida albicans* in the presence of 2% 3ABA-PANI (ES).

FIG. 6 shows a graph of Log 10 reduction of the viable count of *Staphylococcus aureus* ATCC 25923 in the presence of 2% 3ABAPANI (ES)—high initial inoculum.

FIG. 7 shows a graph of Log 10 reduction of the viable count of *Staphylococcus aureus* ATCC 25923 in the presence of 2% 3ABAPANI (ES) and 20% plasma.

FIG. 8 shows a graph of Log 10 reduction of the viable count of *Escherichia coli* ATCC 25922 in the presence of 2% 3ABAPANI (ES) and 20% plasma.

FIG. 9 shows a graph of Log 10 reduction of the viable count of *Pseudomonas aeruginosa* ATCC 27853 in the presence of 2% 3ABAPANI (ES) and 20% plasma.

FIG. 10 shows a graph of Log 10 reduction of the viable count of *Candida albicans* in the presence of 2% 3ABA-PANI (ES) and 20% plasma.

FIG. 11 shows a graph of Log 10 reduction of the viable count of *Candida albicans* in the presence of 2% 3ABA-PANI (ES) and 5% plasma.

FIG. 12 shows a graph of Log 10 reduction of the viable count of *Candida albicans* in the presence of 2% 3ABA-PANI (ES) and 10% plasma.

FIG. 13 shows a graph of Log 10 reduction of the viable count of *Staphylococcus aureus* ATCC 25923 in the presence of 2% 3ABAPANI (ES) and 16 mmol NAC.

FIG. 14 shows Film f4 (PVA and PANI) coated on PMMA after interaction with *Staphylococcus aureus* ATCC 25923.

FIG. 15 shows Film f2 (PVA and Poly3ABA) coated on PMMA after interaction with *Staphylococcus aureus* ATCC 25923.

DETAILED DESCRIPTION OF THE INVENTION

The present invention provides an aniline copolymer for inhibiting growth of microbes.

The invention is particularly useful in preventing or treating nosocomial infections, in particular wound infections and infections associated with medical implants and infections associated with the consumption of food and/or water, although the present invention may be used to target microorganisms in any environment or any type of surface, including but not limited to human and animal subjects or materials to be decontaminated.

Non pathogenic bacteria are also targeted by the present invention, especially where they can cause unwanted effects such as food tainting and spoilage.

The copolymers of the present invention are aniline copolymers, which can be synthesised by reacting aniline with a compound of formula (I)

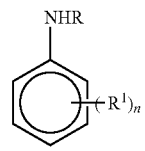

wherein R is hydrogen or a $C_1$-$C_6$ alkyl,
n=1, 2 or 3
$R^1$ is independently selected from the group consisting of:
$C_1$-$C_6$ alkyl,
$C_1$-$C_6$ alkoxyl,
halo,
—$CO_2R^2$,
—$SO_3R^2$,
—$PO_3HR^2$,
—$COR^4$,
—$CH_2COOR^4$,
—CN,
—$CH_2OH$,
—$CH_2NH_2$,
—$CH_2CN$,
—OH,
—$SO_2NH_2$, $R^2$ is selected from hydrogen, $C_1$-$C_6$ alkyl, an alkali metal, ammonium and a substituted ammonium salt;
$R^4$ is selected from hydrogen, $C_1$-$C_6$ alkyl, phenyl; and salts thereof.

The benzene ring may optionally contain one or more hetero atoms in place of a carbon atom, preferably selected from N, O, S, and more preferably one, two or three nitrogen atoms.

In cases where two $R^1$ groups are present, they may be taken together to form a ring, for example if n=2 and both $R^1$ groups are COOH, then the compound may be a phthalic anhydride.

Preferably R is hydrogen and $R^1$ is, $CO_2R^2$, more preferably R is hydrogen and $R^1$ is, $CO_2H$, $CO_2Me$, or, $CO_2Et$. Most preferably formula (I) is a compound selected from the group consisting of 3-aminobenzoic acid, 2-aminobenzoic acid and ethyl 3-aminobenzoate.

When the compound of formula I has n=2, the independently variable $R^1$ groups are preferably, but not necessarily, meta to the NHR group. When the compound of formula I has n=3, the independently variable $R^1$ groups are preferably, but not necessarily, ortho and para to the NHR group.

The copolymer may also be formed by the reaction of aniline with compounds in which the aromatic ring is not be benzenoid, but is any suitable aromatic ring, ie a heterocyclic ring having any number of atoms, more usually 5 or 6. That is, preferably said copolymer is formed by reaction of aniline with a compound of formula Ia,

where R, $R^1$ and n are as above, with Ar being a N-containing heterocycle such as pyridine, pyridazine, pyrimidine, pyrazine, pyrrole, pyrazole, an O-containing heterocycle such as pyran or furan, an S-containing heterocycle such as thiophen, mixed heterocyclic systems such as isoxazole or polycyclic systems such as naphthalene, quinoline or quinoxaline.

Some preferred comonomers include individually or in any combination: 3-acetylaniline; 2-aminobenzaldehyde; 2-aminobenzenesfonamide; 2-aminophenol; 3-aminophenol; 2-aminophenylacetic acid; 3-aminophenylacetic acid; 2-aminobenzonitrile; 3-aminobenzonitrile; 2-aminobenzophenone; 3-aminobenzophenone; 2-aminobenzyl alcohol; 3-aminobenzyl alcohol; 2-aminobenzylamine; 2-aminobenzyl cyanide; 2-amino-4-bromobenzoic acid; 2-amino-6-chlorobenzoic acid; 2-amino-4-chlorobenzoic acid; 2-amino-4-chlorophenol; 2-amino-4-methylphenol; 2-amino-4,6-dihydroxypyrimidine; 2-amino-1,3-diethylbenzene; 1-amino-3,5-dimethylbenzene; 2-amino-4,6-dimethylpyridine; 2-amino-4-hydroxy-6-methylpyrimidine; 5-aminoisophthalic acid; 3-amino-2-methylbenzoic acid; 2-amino-3-methylphenol; 2-amino-6-methylpyridine; 2-amino-3-picoline; 2-aminopyridine; or 3-aminopyridine.

2,6-dimethyl pyridine, 2,4,6-trimethyl pyridine, dimethyl sulfoxide, anhydrous N,N-dimethyl acetamide, tetrahydrofuran and dimethylformamide (DMF) and to a lesser extent by hexafluoro-2-propanol (HFP), chloroform and dichloromethane. The solubilities of PANI, 3ABAPANI (copolymer of 3-amino benzoic acid with aniline), OABAPANI (copolymer of 2-amino benzoic acid with aniline) and 3EABPANI (copolymer of ethyl 3-amino benzoate with aniline) in both ES or EB forms are shown in Table 1. Without being bound by theory it is believed that the copolymers exhibit better solubility in solvents such as N-methyl-2 pyrrolidone (NMP), dimethylformamide (DMF), dimethyl sulfoxide DMSO, tetrahydrofuran (THF) and pyridine due to hydrogen bonding of the solvents with the polymer.

TABLE 1

| Solvent | Solubility[#] | | | | $\epsilon_{max, A}$ | $\epsilon_{max, B}$ | $\epsilon_{max, c}$ |
|---|---|---|---|---|---|---|---|
| | PANI | 3ABA PANI | OABA PANI | 3EAB PANI | | | |
| N-methyl-2 pyrrolidone (NMP) | € | € | € | € | 629 | 327 | — |
| Pyridine | X | € | € | € | 614 | 338 | — |
| 2,6-dimethyl pyridine | X | € | € | € | 621 | 329 | — |
| 2,4,6-trimethyl pyridine | X | € | € | € | 626 | 326 | — |
| Dimethyl sulfoxide | X | € | € | € | 629 | 328 | — |
| N,N-Dimethyl acetamide anhydrous | X | € | € | € | 629/621 | 324 | — |
| Tetrahydrofuran (THF) | X | € | € | € | 580/550 | 313 | 273/290 |
| Dimethylformamide (DMF) | X | € | € | € | 615 | 320 | — |
| Hexafluoro-2-propanol (HFP) | X | ✓X | ✓X | ✓X | 522 | 304 | — |
| Chloroform | X | ✓X | ✓X | ✓X | 561 | 321 | 241 |
| Dichloromethane | X | ✓X | ✓X | ✓X | 547 | 319 | 275 |
| Acetonitrile | X | X | X | X | — | — | — |
| N-methylpyrrolidine | X | X | X | X | — | — | — |
| Acetone | X | X | X | X | — | — | — |
| Ethanol | X | X | X | X | — | — | — |

[#]€ indicates solubility to at least 0.05 mg/mL of solvent;
✓X indicates partial solubility in solvent;
X indicates substantial insolubility in solvent.

The reaction of aniline with a compound of formula (I) is carried out in a mineral acid in the presence of an oxidising agent. Any suitable oxidising agent may be used. Suitable oxidising agents include, although are not limited to ammonium persulphate, potassium ferricyanide, potassium iodate, hydrogen peroxide, cerium (IV) sulphate, potassium dichromate and sodium vanadate. Suitable mineral acids include, although are not limited to hydrochloric acid, sulphuric acid, nitric acid or perchloric acid. Preferably the mineral acid is hydrochloric acid and the oxidising agent is potassium iodate $KIO_3$.

The copolymers of the present invention were synthesized using a reaction mixture with a 1:1 mole ratio of aniline to functionalised aniline, which resulted in good yields and produced products with enhanced solubility, relative to PANI, in common organic solvents, which include but are not limited to N-methyl-2-pyrrolidone (NMP), pyridine, The aniline copolymers of the present invention are substantially insoluble in water, and are stable to wet heat sterilization at 121° C.

A lower yield, 20-25% of product, was obtained from reaction mixtures with a lower proportion of aniline relative to functionalised aniline (1:2). A 2:1 mole ratio of aniline to functionalised aniline showed lower solubility in common organic solvents. The comonomer reactivity ratios for aniline and either 2-aminobenzoic acid or 3-aminobenzoic acid indicate that the corresponding copolymer chains should have about 90% aniline units and 10% functionalised aniline units. The ratio of the aniline and functionalised aniline units in the copolymers is governed by comonomer reactivity ratios and the relative proportions of the comonomers in the reaction mixtures.

Even with a small proportion (for example about 10%) of functionalised aniline units in the copolymer chains properties such as solubility in organic solvents are significantly changed when compared with PANI. Preferably the copolymer contains at least about 0.01% functionalised aniline units, more preferably at least about 1% functionalised aniline units, most preferably at least about 10% functionalised aniline units.

Homopolymers of functionalised anilines are often undesirable as these usually have some solubility in water, which is unwanted for some industrial applications. Functional anilines also tend to be less reactive than aniline itself in polymer formation.

Due to the relative values of the reactivity ratios (aniline>functionalised aniline), the copolymers have longer sequences of aniline units, on average, than of functionalised aniline units. The functionalised anilines can be randomly distributed in the copolymer chains or they can form block copolymers. Typically the functionalised anilines are randomly distributed.

By changing the ratio of aniline to functionalized aniline different colours of copolymers can be obtained for less than 10-15% of aniline presented in the starting mixture.

Whilst the arrangement of atoms is unchanged in the copolymer chain, the electronic structure of the copolymers of aniline and 2-amino benzoic acid is known to be dependent upon the copolymer's oxidation state. The structures of PANT, as shown below, are leucoemeraldine (totally reduced), emeraldine (half oxidised) and pernigraniline (fully oxidised).

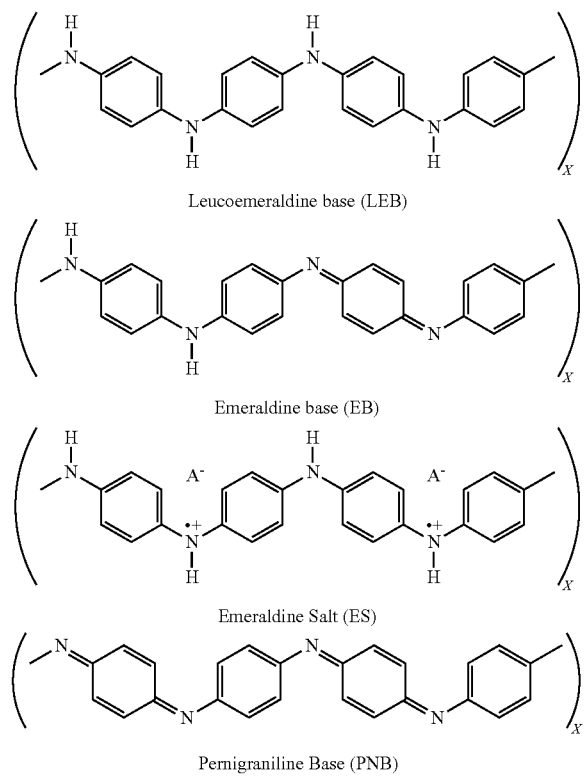

Leucoemeraldine base (LEB)

Emeraldine base (EB)

Emeraldine Salt (ES)

Pernigraniline Base (PNB)

X indicates the degree of polymerisation, A is an anion.

The emeraldine forms can be isolated as its salt (ES) or base (EB) form. The EB form can be obtained from its salt (ES) by addition of a base. Preferably the base is a 1-15% (typically 6%) ammonia solution. Other suitable bases include, although are not limited to metal hydroxides, such as sodium hydroxide and lithium hydroxide.

The aniline copolymers of the present invention also demonstrate antioxidant activity. In combination with their antibacterial properties, this makes them particularly useful in the field of food packaging and preservation. The workability of the polyanilines of the present invention means they can be incorporated into cling film wraps, bags and the like. The presence of functional groups can further enable the aniline copolymers to be covalently linked into other film forming components if desired. The conducting polymers therefore have potential application as antioxidants in the food and rubber industries. Oxidation is the main cause of deterioration of foodstuffs.

Conducting polymer antioxidants may also be employed to inhibit uncontrolled oxidation of lipids, proteins and DNA in biological systems, which are important in the progression of various diseases, cancer and aging.

Scavenging of free radicals is a property that is widely regarded as beneficial for compounds that are likely to be present, or to come into contact with, biological tissues. The various vitamin and polyphenol free radical scavenging antioxidants present in beverages, fruits and vegetables are currently of great interest due to the protection they may afford against various diseases, such as cardio-vascular diseases and cancer. Their mechanisms of action, while still to be fully confirmed, include the chelation of pro-oxidant metal ions, and the ability to scavenge, by their action as reducing agents, excessive levels of damaging free radicals, which otherwise contribute to the oxidation and degradation of lipid material and DNA.

Aniline copolymers in their emeraldine salt form typically show better radical scavenging than emeraldine base forms.

The service requirements of finished rubber products demand improved polymer stabilization. Oxidative aging of rubber is one of the most important problems in rubber technology because the absorption of a small amount of oxygen by rubber causes a considerable change in its physicomechanical properties. Such changes can be retarded but not completely avoided by the addition of antioxidants. Polyanilines were shown to be efficient in slowing down the rate of oxidation, particularly when a methoxy-substituted polyaniline was used.

The aniline copolymers of the present invention are useful against a wide variety of bacteria, including both pathogenic and non pathogenic varieties. Aniline copolymers in their emeraldine salt forms show better antimicrobial activities than emeraldine base forms.

Bacteria which are target organisms of the present invention can be aerobic, anaerobic, facultatively anaerobic or microaerophilic. Gram-negative aerobic and microaerophilic rods and cocci include the genera *Bordetella*, *Neisseria*, and *Legionella*. Facultatively anaerobic Gram-negative rods include genera *Pseudomonas*, *Salmonella*, *Shigella*, *Erwinia*, *Enterobacter*, *Escherichia*, *Vibrio*, *Haemophilus*, *Actinobacillus* and *Klebsiella*. An important group of bacteria as target organisms for the present invention are the Gram-positive aerobic and microaerophilic rods and cocci that include the genera *Staphylococcus*, *Streptococcus*, *Enterococcus*, *Corynebacterium*, *Listeria*, *Bacillus* and *Erysipelothrix*. Bacteria that are particularly targeted by the present invention include *Staphylococcus aureus*, *Escherichia coli*, *Pseudomonas aeruginosa*, *Salmonella enterica* serotype *Enteritidis*, *Enterococcus* sp., *Staphylococcus sciuri*, *Enterobacter* sp. and *Campylobacter jejuni*.

Additional bacterial genera include: *Mycobacterium*, *Leptospira*, *Serpulina*, *Mycoplasma*, *Bacteroides*, *Yersinia*, *Chlamydia*, *Porphyromonas*, *Hemophilus*, *Pasteurella*, *Peptostreptococcus*, *Propionibacterium*, *Dermatophilus*. These and other bacterial groups and genera not listed here will be recognized by the skilled artisan as suitable target bacteria for the present invention.

The compositions of the present invention are particularly useful in treating skin infections, in particular superficial skin infections caused by various bacteria. Fungal genera which are targeted by the aniline copolymers of the present inventions include, but are not limited to those genera selected from the group consisting of *Aspergillus, Blastomyces, Candida, Coccudioides, Cryptococcus, Epidermophyton, Histoplasma, Microsporum, Mucor, Rhizopus, Sporothrix, Trichophyton, Paracoccidioides, Absidia, Fusarium, Penicillium, Torulopsis, Trichosporon, Rhodotorula, Malassezia, Cladosporium, Fonsecea* and *Phialophora*.

DNA viruses and said RNA viruses include families selected from the group consisting of Parvoviridae, Papillomaviridae, Polyomaviridae, Adenoviridae, Hepadnaviridae, Herpesviridae, Poxviridae, Picornaviridae, Caliciviridae, Reoviridae, Togaviridae, Flaviviridae, Coronaviridae, Orthomyxoviridae, Paramyxoviridae, Rhabdoviridae, Filoviridae, Bunyaviridae, Arenaviridae and Retroviridae.

The above bacteria, fungi and viruses are illustrative suitable target organisms, but the invention is not to be considered limited to the species, genera, families, orders or classes listed.

Three aniline copolymers, 3ABAPANI (the 1:1 copolymer of 3-amino benzoic acid with aniline), OABAPANI (the 1:1 copolymer of anthranilic acid with aniline) and 3EABPANI (the 1:1 copolymer of ethyl 3-aminobenzoate with aniline) in both ES or EB forms were tested for their antibacterial properties. All three show greater effectiveness as antibacterial agents than PANI itself.

The ES forms of copolymers appear to be more effective than EB forms of the same copolymer. 3ABAPANI and OABAPANI copolymers showed better inhibitory effect against microorganisms than 3EABPANI. It appears that the presence of an acidic functional group (ie., COOH) in the polymer chain improves the antibacterial efficacy of the copolymer. Without being bound by theory, the acidic dopants on the molecular chains of copolymers may react with the bacteria (or other relevant microbial organism) which result in their death. Alternatively, due to electrostatic adherence between copolymer molecules and the bacteria, which carry charges of different polarity, the walls of bacteria may break and the contents of bacteria become exposed or leak out, which cause the bacteria to die.

Aniline copolymers can be applied to a surface as a solid, or in liquid form.

Aniline copolymers can be incorporated into conventional polymer films, which can be applied to a surface. Conventional polymer films include, although are not limited to poly(vinyl alcohol), polyethylene, polypropylene, poly(ethylene terephthalate), poly(vinylidene fluoride), butene copolymers, hexene copolymers, methyl acrylate copolymers and ethylene vinyl acetate copolymers.

Aniline copolymers can be used in the manufacture of antibacterial and/or antifungal and/or antiviral objects. Such objects include, although are not limited to medical dressings, urine catheters, endoscopes, medical instruments, hospital furniture, masks, floors, food packets, plastic film wraps, food processing surfaces and apparatus, pipettes, computer keyboards and mouses, cosmetics, handles, water tanks, membranes for water purification, toilets, door handles, drainage pipes, water pipes, ear pieces, shoe insoles, pools, bags for urine or feces or blood platelets, air-conditioning units, filtration equipment, pasteurization equipment and furniture.

Aniline polymers can be used in a variety of industries known to the skilled artisan. Such industries include although are not limited to the health industry, food industry, packaging industry, water industry, paint industry, textile industry, plastic industry, glass industry, paper industry, rubber industry, ceramic industry, wood industry, poultry industry, seafood industry, sports industry and agricultural industry.

EXAMPLES

Synthesis of Copolymers.

The 1:1 copolymer synthesis of aniline with 3-amino benzoic acid (3ABAPANI) or aniline with anthranilic acid (OABAPANI) was performed using 3.88 mL aniline, 5.85 g 3-amino benzoic acid or anthranilic acid respectively, 8.64 g of potassium iodate ($KIO_3$) and 240 mL of 1.25 M hydrochloric acid.

The 1:1 copolymer synthesis of aniline with ethyl 3-amino benzoate (3EABPANI) was carried out using 0.9 mL of aniline, 1.65 g of ethyl 3-aminobenzoate, 62.5 mL of 1.25 M HCl and 2.25 g of $KIO_3$.

After cooling the solution of potassium iodate and hydrochloric acid at 7° C., aniline and functionalised aniline monomers were used in 1:1 mole ratio. The solution was stirred for 5 hours at 7° C. to obtain emeraldine salt (ES) form. The reaction mixture was filtered and washed thoroughly with distilled water and the filtrate was transferred to a flask and stirred overnight with 150 mL (or 46.8 mL in the case of 3EABPANI) of 6% ammonia solution to dedope the polymer and obtain the emeraldine base (EB) form. Only half the amount of the ES form of each copolymer was used to prepare the EB form. After filtering and washing repeatedly with distilled water, the filtrate was stirred for 15 minutes with 75 mL (or 23.5 mL in the case of 3EABPANI) of acetone and filtered again. The ES form of each copolymer was also purified with acetone under the same conditions as for the EB forms. The filtrate of each copolymer (EB or ES) was left to dry in a vacuum oven at 40° C. overnight.

Without wishing to be bound by theory, it is believed that the treatment with acetone serves to wash out unreacted or incompletely reacted starting materials (e.g. monomers) or intermediates (e.g. oligomers) which may have undesirable toxic side effects. Acetone is a preferred compound for this purpose, but some other suitable solvent could be used. The antimicrobial activity of the polyaniline was not observed to diminish following this treatment.

To compare antimicrobial and antioxidant abilities of 3ABAPANI, OABAPANI and 3EABPANI samples, the copolymers of aniline with functionalized aniline (—$OCH_3$, —$CH_3$, —$SO_3H$, —Cl) in ES forms were synthesised under the same conditions as for 3ABAPANI/OABAPANI (ES) samples. Homopolymers of functionalized anilines, 3-amino benzoic acid (Poly 3ABA) and 3-aminosulfonic acid (Poly $SO_3H$) were also chemically synthesised.

FTIR

EB form of PANI has strong absorption peaks at 1586, 1493, 1305, 1162 and 828 $cm^{-1}$. The shifting of bands due to quinoid units from 1586 $cm^{-1}$ and 1162 $cm^{-1}$ to 1574 $cm^{-1}$ and 1135 $cm^{-1}$, respectively were observed in protonated salt form (ES) of PANI.

The characteristic band due to carbonyl group C=O was observed in all copolymer samples, with the higher intensity in ES forms. The $NH^+$ structure in ES forms of copolymers was confirmed with the band appearing at 1135 cm$^{-1}$. The bands at 1220, 1105, 1010 and 830 cm$^{-1}$ arise from 1,4 substitution of benzenoid ring. Also bands due to functionalised aniline were found in both ES and EB forms of copolymers.

Raman

The Raman spectra showed similar bands to those for PANI ES and EB forms. The appearance of the band at 1336 cm$^{-1}$ in ES form of copolymers is assigned to C—N stretching of the cation radical species. Amine deformation band for ES, N—H bending at 1414 cm$^{-1}$ was also observed.

UV-VIS

There are two characteristic peaks in the UV-VIS spectrum of PANI/NMP solutions: the peak at ~330 nm (referred to as the benzenoid peak; B) and a second peak at ~630 nm (referred to as the quinoid peak; Q). Better solubility is shown by 3EABPANI samples.

Radical Scavenging Ability

The DPPH free radical scavenging activity of copolymers and the ratio of aniline units per DPPH radical scavenged for each copolymer are presented in Table 2.

TABLE 2

| Sample | DPPH scavenged by copolymer (†mol) | †mol of aniline units for 1 mg of copolymer | Ratio of aniline units per DPPH radical scavenged |
| --- | --- | --- | --- |
| 3ABAPANI (ES) | 3.1 | 10.5 | 3.4 |
| OABAPANI (ES) | 3.1 | 10.5 | 3.4 |
| 3EABPANI (ES) | 1.7 | 10.2 | 6.0 |
| SO$_3$HPANI (ES) | 3.1 | 10.4 | 3.4 |
| Cl PANI (ES) | 1.3 | 10.6 | 8.2 |
| CH$_3$PANI (ES) | 2.2 | 10.8 | 4.9 |
| OCH$_3$PANI (ES) | 2.4 | 10.4 | 4.3 |

Copolymers with an acidic functional group show better radical scavenging ability than copolymers without an acidic functional group. The extent of DPPH scavenging by 3ABAPANI/OABAPANI copolymer and 3EABPANI is 3.1 and 1.7 †mol, respectively. The DPPH scavenging activity is approximately two times higher for 3ABAPANI/OABAPANI than for 3EABPANI samples. The copolymers with a strongly acidic group (—SO$_3$H) present in the polymer chain show the same DPPH activity as the copolymers with the more weakly acidic, COOH group. Moreover, the DPPH activity of copolymers with a, COOH substituent was independent of the position (ortho or meta) of the substituent. Thus using the largest scavenging values for each copolymer, a ratio of 3.4 aniline units per DPPH radical scavenged was obtained for 3ABAPANI/OABAPANI/SO$_3$HPANI, which increased to 8.2 aniline units for Cl PANI.

Bacteria.

Compounds of the present invention were tested against the following bacterial strains: *Staphylococcus aureus* ATCC 25923 (ATCC=American Type Culture Collection) (Gram-positive bacterium), *Escherichia coli* ATCC 25922 (Gram-negative bacterium), *Pseudomonas aeruginosa* ATCC 27853 (Gram-negative bacterium), *Salmonella enterica* serotype Enteritidis (strain resistant to two antibiotics; Gram-negative bacterium), *Enterococcus faecalis* (vancomycin resistant strain; Gram-positive bacterium), *Staphylococcus sciuri* (oxacillin resistant strain and multi drug resistant; Gram-positive bacterium), *Enterobacter* sp. (multi drug resistant strain; Gram-negative bacterium), *Pseudomonas aeruginosa* (multi drug resistant strain; Gram-negative bacterium), *Campylobacter jejuni* (strain A; Gram-negative bacterium), *Campylobacter jejuni* (strain B; Gram-negative bacterium), *Salmonella enterica* serotype Enteritidis (extended spectrum beta lactamase positive isolate and multi drug resistant; Gram-negative bacterium), *Escherichia coli* (extended spectrum beta lactamase positive isolate and multi drug resistant; Gram-negative bacterium), *Pseudomonas aeruginosa* (metallo beta lactamase positive and multi drug resistant; Gram-negative bacterium), *Staphylococcus aureus* (methicillin resistant and multi drug resistant; Gram-positive bacterium), *Listeria monocytogenes* ATCC BAA-751 (Gram-positive bacterium), *Bacillus subtilis* ATCC 6633 (Gram-positive bacterium) and *Enterococcus faecalis* ATCC 29212 (Gram-positive bacterium).

The stock cultures of the strains were maintained in tryptic soy broth (bioMèrieux, France) supplemented with 15% of glycerol at −80° C. The only exceptions were two *Campylobacter jejuni* strains, which were used as fresh isolates.

The strains were transferred from the stock culture onto brain heart infusion (BHI) agar (BD-Becton Dickinson Microbiology Systems, USA), and incubated overnight at 35° C., in air atmosphere. The only exceptions were two *Campylobacter jejuni* strains, which were cultured on BHI agar supplemented with 5% horse blood, and incubated for 2 days at 35° C., in microaerophilic conditions obtained with GENbox microaer system (bioMèrieux, France). The strains were subcultured one more time under the same conditions, and the grown cultures were used for preparation of bacterial suspensions equal to 0.5 McFarland (~10$^8$ cfu/mL; cfu/mL=colony forming units per mL), with sterile cotton swabs, in 5 mL of suspension medium (bioMèrieux, France) by using Densimat densitometer (bioMèrieux, France), and were further diluted as required.

The antibacterial activity of copolymers was tested as a) copolymer dispersed in polyvinyl alcohol (PVA) films, and b) pure powders. The copolymer/PVA film was mixed, sterilized in autoclave at 121° C. for 15 minutes, and poured in Petri-plates. Incubation at 35° C. for 48 h was used to evaporate water from the copolymer/PVA film. 3ABAPANI (0.2 wt %) in PVA was tested with different amounts (10$^6$, 10$^5$, 10$^4$ and 10$^3$ cfu/mL) of Gram-negative *Escherichia coli* ATCC 25922 and Gram-positive *Staphylococcus aureus* ATCC 25923 bacteria. The suspension of bacteria (100 µL) was poured above the dried copolymer/PVA film, and thereafter overlaid with Brain-Heart Infusion agar. The plates were incubated at 35° C. for 48 h before the reading of the results.

Yeasts and Moulds.

Compounds of the present invention were tested against the following yeast and mold strains: *Candida albicans, Cryptococcus neoformans, Candida guilliermondii, Candida parapsilosis, Candida kefyr, Candida glabrata, Aspergillus flavus*, and *Aspergillus niger*.

The yeast strains were transferred from the stock culture onto Saboraud dextrose agar (SDA) agar (bioMèrieux, France), and incubated overnight at 35° C., in an air atmosphere. The yeast strains were subcultured once again under the same conditions, and the grown cultures were used for preparation of yeast suspensions equal to 0.5 McFarland (1-5×10$^6$ cfu/mL; cfu/mL=colony forming units per mL, i.e. number of yeasts per mL), by using Densimat densitometer (bioMèrieux, France), and were further diluted as required.

The moulds were transferred from the stock culture onto Saboraud dextrose agar (SDA) (bioMèrieux, France), and incubated 5 days at 35° C., in an air atmosphere. Moulds were subcultured once again under the same conditions, and the cultures were used for preparation of inoculum suspensions by covering the surface of *Aspergillus* colonies with 5 mL of BHI broth containing Tween-20 0.1% v/v and probing with a sterile loop. The conidia suspensions were transferred to a sterile tube, shaken vigorously by vortexing, and then adjusted by microscopic enumeration with a Neubauer cell-counting haemacytometer to provide a suspension of 1-5× $10^6$ conidia/mL. The suspensions were diluted as required. Minimum Inhibitory Concentration (MIC).

The MIC for copolymer powders was determined using the microdilution assay, which was performed in sterile flat-bottomed 96-well polystyrene non-tissue culture treated microtiterplate (microplate) with a lid in a final volume of 100 †L as follows.

Forty mg (40 mg=0.04 g) of copolymer or pure chemically synthesised polyaniline, used as a reference material (PANI) was weighed on an analytical balance in a glass tube, and 2 mL of BHI broth (bioMèrieux, France) was added to obtain 2% suspension of copolymers or PANI. Thereafter copolymer or PANI suspension was sterilized at 121° C. for 15 min in an autoclave (using water-saturated steam under pressure).

After sterilization 100 µL of copolymer or PANI suspension was added, with automatic pipette, per well, in triplicate (three wells per copolymer or PANT). Thereafter 50 µL of BHI broth was added to all empty wells, and in total seven twofold dilutions of copolymer or polyaniline suspensions (2%-1%-0.5%-0.25%-0.125%-0.0625%-0.03125%) were made by transferring 50 µL from one well to another (starting with the first well, which contained 100 µL of copolymer or PANI suspension) by automatic pipette. After this step all wells 5 contained 50 µL of fluid. The bacterial suspension equal to 0.5 McFarland (~108 cfu/mL) was two times 10-fold diluted in BHI broth to obtain ~106 cfu/mL, while yeast and mold suspensions were once 10-fold diluted in BHI broth. Fifty microliters (50 µL) of BHI broth containing diluted microorganisms were added to 50 µL of copolymer or PANI suspensions made in BHI broth (i.e. polyaniline suspensions were one more time twofold diluted, as well as suspension of microorganisms). Therefore the final concentrations of copolymer or PANI in wells ranged from 1%-0.5%-0.25%-0.125%-0.0625%-0.03125%-0.015625%, while the final bacterial inoculum contained ~5×105 cfu/mL and final yeast and mold inoculum contained 0.5-2.5×105 cfu/mL. Wells containing only BHI broth and bacteria and/or yeast/mold (without copolymer or PANI), were used as the growth control.

Microtiterplates were covered with their lids and incubated for 2 days at 35° C., in air atmosphere, before reading the results. Microtiterplates with *Campylobacter jejuni* strains were incubated in ajar under the microaerophilic conditions obtained with GENbox microaer system (bioMèrieux, France).

The minimal inhibitory concentration (MIC) was defined as the lowest concentration of an aniline copolymer or polyaniline preventing visible turbidity, as determined by naked eye.

The results obtained from testing the antimicrobial activity of copolymer dispersed in polyvinyl alcohol (PVA) films were similar to the results obtained from testing pure powders for ~$10^6$ cfu/mL. Pure PVA films had no antibacterial effect. However, the copolymer/PVA films cannot keep uniform dispersion of copolymer over PVA due to PVA dissolving in water (major component of nutritious base is water, 95-98 wt %). Table 3 shows the results (wt %) for each sample for inhibitory effect on each type of tested bacteria.

Table 4 shows the inhibitory effect (wt %) on specific bacteria types by certain substituted polyanilines.

The copolymers were most effective on *Campylobacter jejuni* bacteria. All three copolymers, 3ABAPANI, OABAPANI and 3EABPANI in both ES or EB forms showed greater effectiveness as antibacterial agents than pure chemically synthesised PANI and the copolymers $OCH_3PANI$, $CH_3PANI$ and ClPANI. ES forms of copolymers were in all cases more effective than EB forms of the same copolymer.

Table 5 shows the results (wt %) for each sample for inhibitory effect on each type of tested yeast and mould.

No difference in antimicrobial activity was found between 3ABAPANI and OABAPANI (—COOH in 3 or 2 position). Copolymer with strongly acidic group (—$SO_3H$ in $SO_3HPANI$ copolymer) showed similar antimicrobial activity to copolymer with, COOH (3ABAPANI/OABAPANI). Similar results were obtained from testing antioxidant properties of 3ABAPANI, OABAPANI and $SO_3HPANI$.

All three copolymers, 3ABAPANI, OABAPANI and 3EABPANI, were active against antibiotic resistant bacteria, including multi drug resistant bacteria, vancomycin resistant *enterococcus* and methicillin/oxacillin resistant *staphylococcus*, as well as yeasts and moulds.

It will be appreciated that the illustrated aniline copolymers are soluble in common organic solvents and have antibacterial and antifungal activity.

TABLE 3 (a)

| Sample | S. aureus ATCC 25923 (wt %) | E. coli ATCC 25922 (wt %) | P. aeruginosa ATCC 27853 (wt %) | Salmonella (wt %) MDR | Enterobacter (wt %) MDR | E. faecalis (wt %) VR, MDR |
|---|---|---|---|---|---|---|
| 3ABA PANI (ES) | 0.125 | 0.125 | 0.25 | 0.5 | 0.5 | 0.5 |
| OABA PANI (ES) | 0.125 | 0.125 | 0.25 | 0.5 | 0.5 | 0.5 |
| 3EAB PANI (ES) | 0.5-1 | 0.5 | 0.5-1 | 0.5-1 | 1 | 1 |
| PANI (ES) | 1 | 1 | >1 | >1 | >1 | >1 |
| 3ABA PANI (EB) | 0.25 | 0.5 | 0.5 | 0.5-1 | 0.5-1 | 0.5-1 |
| OABA PANI (EB) | 0.25 | 0.5 | 0.5 | 0.5-1 | 0.5-1 | 0.5-1 |
| 3EAB PANI (EB) | 1 | 0.5-1 | 1 | 1 | 1 | 1 |
| PANI (EB) | >1 | 1 | >1 | >1 | >1 | >1 |

TABLE 3 (b)

| Sample | P. aeruginosa (wt %) MDR | S. ciuri (wt %) MR, MDR | C. jejuni (A) (wt %) | C. jejuni (B) (wt %) | Salmonella (wt %) ESBL positive; MDR | E. coli (wt %) ESBL positive; MDR |
|---|---|---|---|---|---|---|
| 3ABA PANI (ES) | 0.25 | 0.5 | 0.03125 | 0.03125 | 0.5 | 0.5 |
| OABA PANI (ES) | 0.25 | 0.5 | 0.03125 | 0.03125 | 0.5 | 0.5 |
| 3EAB PANI (ES) | 0.5-1 | 1 | 0.0625 | 0.0625 | 1 | 1 |
| PANI (ES) | >1 | >1 | 0.25 | 0.25 | >1 | >1 |
| 3ABA PANI (EB) | 0.5 | 1 | 0.5 | 0.5 | 1 | 1 |
| OABA PANI (EB) | 0.5 | 1 | 0.5 | 0.5 | 1 | 1 |
| 3EAB PANI (EB) | 1 | 1 | 0.5-1 | 0.5-1 | 1 | 1 |
| PANI (EB) | >1 | >1 | 1 | 1 | >1 | >1 |

TABLE 3 (c)

| Sample | P. aeruginosa (wt %) MBL positive; MDR | S. aureus (wt %) MR, MDR | L. Monocytogenes (wt %) | B. Subtilis (wt %) | E. faecalis (wt %) |
|---|---|---|---|---|---|
| 3ABAPANI (ES) | 0.25-0.5 | 0.25-0.5 | 0.25 | 0.25 | 0.25-0.5 |
| OABAPANI (ES) | 0.5 | 0.5 | 0.5 | 0.25-0.5 | 0.25-0.5 |
| 3EABPANI (ES) | 1 | 0.5-1 | 0.5-1 | 0.5 | 0.5 |
| PANI (ES) | >1 | 1 | 1 | >1 | 1 |
| 3ABAPANI (EB) | 1 | 0.5 | 0.5 | 0.5 | 0.5-1 |
| OABAPANI (EB) | 1 | 0.5-1 | 0.5 | 0.5-1 | 0.5-1 |
| 3EABPANI (EB) | 1 | 1 | 1 | 1 | 1 |
| PANI (EB) | >1 | >1 | >1 | >1 | >1 |

[The ES forms were also purified with acetone washing prior to testing and their activities were unchanged from the results shown here for samples not pre-purified with acetone.]

*MDR=multidrug resistance i.e. resistance to three or more antimicrobial agents with different mechanism of action; ESBL=extended spectrum beta lactamase; MBL=metallo beta lactamase; VR=vancomycin resistant; MR=methicillin/oxacillin resistant.

TABLE 4 (a)

| Sample | S. aureus ATCC 25923 (wt %) | E. coli ATCC 25922 (wt %) | P. aeruginosa ATCC 27853 (wt %) | Salmonella (wt %) ESBL positive; MDR | E. faecalis (wt %) VR, MDR | S. ciuri (wt %) MR, MDR | C. jejuni (A) (wt %) |
|---|---|---|---|---|---|---|---|
| SO₃HPANI (ES) | 0.25 | 1 | 1 | 1 | 1 | 0.5-1 | 0.5 |
| C1PANI (ES) | 1 | 0.5 | 1 | 1 | >1 | >1 | 0.5 |
| CH₃PANI (ES) | 1 | >1 | >1 | >1 | >1 | >1 | >1 |
| OCH₃PANI (ES) | 0.5 | >1 | >1 | >1 | >1 | 1 | 0.5 |
| Poly 3ABA | 0.25 | 0.25 | 0.5 | 0.25 | 0.5 | 0.25 | 0.06 |
| Poly SO₃H | 0.5 | 0.5 | 0.5 | 0.5 | 0.5 | 0.25 | 0.25 |

TABLE 4 (b)

| Sample | C. jejuni (B) (wt %) | E. coli (wt %) ESBL positive MDR | P. aeruginosa (wt %) MBL positive; MDR | S. aureus (wt %) MR, MDR | L. Monocytogenes (wt %) | B. Subtilis (wt %) | E. faecalis ATCC 29212 (wt %) |
|---|---|---|---|---|---|---|---|
| SO₃HPANI (ES) | 0.5 | 1 | 1 | 1 | 1 | 1 | 1 |
| C1PANI (ES) | 0.5 | 1 | >1 | >1 | >1 | >1 | >1 |
| CH₃PANI (ES) | >1 | >1 | >1 | >1 | >1 | >1 | >1 |
| OCH₃PANI (ES) | 0.5 | .1 | >1 | 1 | 1 | 1 | 1 |
| Poly 3ABA | 0.06 | 0.25 | 0.25-0.5 | 0.25 | 0.25 | 0.25 | 0.5 |
| Poly SO₃H | 0.25 | 0.5 | 0.5 | 0.5 | 0.5 | 0.5 | 0.5 |

*MDR = multidrug resistance i.e. resistance to three or more antimicrobial agents with different mechanism of action;
ESBL = extended spectrum beta lactamase;
MBL = metallo beta lactamase;
VR = vancomycin resistant;
MR = methicillin/oxacillin resistant.

TABLE 5 (a)

| Sample | Candida albicans | Cryptococcus neoformans | Candida guilliermondii | Candida parapsilosis |
|---|---|---|---|---|
| 3ABAPANI (ES) | 0.5-1 | 0.5-1 | 0.5 | 1 |
| OABAPANI (ES) | 0.5-1 | 0.5-1 | 0.5-1 | 1 |
| 3EABPANI (ES) | 1 | 1 | 1 | >1 |

TABLE 5 (a)-continued

| Sample | Candida albicans | Cryptococcus neoformans | Candida guilliermondii | Candida parapsilosis |
|---|---|---|---|---|
| PANI (ES) | >1 | >1 | >1 | >1 |
| 3ABAPANI (EB) | 1 | 1 | 1 | >1 |
| OABAPANI (EB) | >1 | >1 | >1 | >1 |
| 3EABPANI (EB) | >1 | >1 | >1 | >1 |
| PANI (EB) | >1 | >1 | >1 | >1 |
| SO$_3$HPANI (ES) | 1 | 0.5-1 | 1 | >1 |
| ClPANI (ES) | >1 | >1 | >1 | >1 |
| CH$_3$PANI (ES) | >1 | >1 | >1 | >1 |
| OCH$_3$PANI (ES) | 1 | 0.5-1 | 0.5-1 | 1 |
| Poly 3ABA | 1 | 0.5 | 0.5 | 1 |
| Poly SO$_3$H | >1 | >1 | >1 | >1 |

TABLE 5 (b)

| Sample | Candida kefyr | Candida glabrata | Aspergillus flavus | Aspergillus niger |
|---|---|---|---|---|
| 3ABAPANI (ES) | 0.5-1 | 1 | 0.5-1 | 1 |
| OABAPANI (ES) | 0.5-1 | 1 | 1 | 1 |
| 3EABPANI (ES) | 1 | >1 | 1 | >1 |
| PANI (ES) | >1 | >1 | >1 | >1 |
| 3ABAPANI (EB) | 1 | >1 | 1 | >1 |
| OABAPANI (EB) | >1 | >1 | >1 | >1 |
| 3EABPANI (EB) | >1 | >1 | >1 | >1 |
| PANI (EB) | >1 | >1 | >1 | >1 |
| SO$_3$HPANI (ES) | 1 | 1 | >1 | >1 |
| ClPANI (ES) | >1 | >1 | >1 | >1 |
| CH$_3$PANI (ES) | >1 | >1 | >1 | >1 |
| OCH$_3$PANI (ES) | >1 | 1 | 1 | 1 |
| Poly 3ABA | 0.5 | 1 | 0.5-1 | 1 |
| Poly SO$_3$H | >1 | >1 | >1 | >1 |

Mechanism of Action.

FTIR spectra of 3ABAPANI (ES), 3EABPANI (ES), OABAPANI (ES), PANI (ES), SO$_3$HPANI (ES), 3ABA-PANI (EB) and PANI (EB) after sterilization and treatment with a) Gram-negative *Escherichia coli* ATCC 25922 and *Pseudomonas aeruginosa* ATCC 27853 and b) Gram-positive *Staphylococcus aureus* ATCC 25923 bacteria were recorded. The results show C—C stretching quinoid and deprotonated band shifts up to 9 cm$^{-1}$ in all samples. Without wishing to be bound by theory, these results suggest that due to electrostatic adherence between polymer molecules and microorganism e.g. *E. coli* bacteria (as an example), which carry charges of different polarity, the walls of bacteria break and the contents of the bacteria leak out, as shown in FIG. 1, which makes the bacteria die.

The EPR signal increased after interaction with bacteria in all samples. These results imply that the concentration of polarons in the polymer chains increased after interaction with bacteria which is another confirmation that electrostatic adherence happened between aniline copolymers and bacteria.

Agar Diffusion Method•Tablets.

Tablets 1.5 cm in diameter with average weight 100±5 mg were made from the copolymers listed in Table 6 below. The antimicrobial activity was tested on *Staphylococcus aureus* ATCC 25923.

BHI agar, 20 mL, was poured into a 90 mm Petri plate. A suspension of *Staphylococcus aureus* ATCC 25923 equal to 0.5 McFarland was inoculated by cotton swabs onto BHI agar. Thereafter tablets were placed on the inoculated surface of BHI agar. The plates were incubated overnight at 35° C., in air. The size of the inhibition zone, in mm, was measured around each tablet.

TABLE 6

| Sample | Size of the inhibition zone (mm) (includes 15 mm tablet size) |
|---|---|
| 3ABAPANI (ES) | 52 |
| 3EABPANI (ES) | 29 |
| OABAPANI (ES) | 48 |
| PANI(ES) | 20 |
| SO$_3$HPANI (ES) | 46 |
| ClPANI (ES) | 22 |
| CH$_3$PANI (ES) | 32 |

The greater effectiveness of the copolymers of the present invention as antibacterial agents over pure chemically synthesised PANI was noted for all copolymer samples. Copolymers with strongly acidic groups, such as 3ABAPANI, OABAPANI and SO$_3$HPANI (ES) showed a strong inhibition zone.

Mechanism of Action: Inhibitory Effect Vs Bactericidal/Fungicidal Effect.

A "static" or "inhibitory" effect means that agent/substance inhibits the growth of microorganisms, while bactericidal/fungicidal/viricidal means that agent/sub stance kills microorganisms. The mechanism of action was determined for 3ABAPANI (ES) and PANI (ES) against the bacteria *Staphylococcus aureus* ATCC 25923, *Escherichia coli* ATCC 25922, *Pseudomonas aeruginosa* ATCC 27853 and the yeast *Candida albicans*.

Suspensions containing 2%, 1%, 0.5%, 0.25% and 0.125% of 3ABAPANI (ES) and PANI (ES) were made in 2 mL of BHI broth, in glass tubes, and sterilized at 121° C. in an autoclave. Thereafter suspensions were inoculated with microorganisms, to obtain 5×10$^5$ cfu/mL of bacteria, and 0.5-2.5×10$^5$ cfu/mL of yeast. After 24 h incubation 100 μL from all tubes was transferred to BHI agar plate, and spread over the BHI agar surface with a glass rod. After incubation of the BHI agar plates for 48 h at 35° C., the microorganism colonies were counted. If no more than 0.1% of microorganisms of the initial microorganism inoculum (99.9% killing) survived, the sample was considered to be bactericidal (or fungicidal, in the case of *Candida albicans*).

TABLE 7

| Microorganism | 3ABAPANI (ES) The lowest concentration which kills microorganisms (wt %) | PANI (ES) The lowest concentration which kills microorganisms (wt %) |
|---|---|---|
| *Staphylococcus aureus* ATCC 25923 | 0.5 | 1 |
| *Escherichia coli* ATCC 25922 | 0.5 | —* |

TABLE 7-continued

| Microorganism | 3ABAPANI (ES) The lowest concentration which kills microorganisms (wt %) | PANI (ES) The lowest concentration which kills microorganisms (wt %) |
|---|---|---|
| *Pseudomonas aeruginosa* ATCC 27853 | 0.5 | 1 |
| *Candida albicans* | 2 | —* |

*static effect was noted, possibly cidal in higher concentrations.

This experiment confirmed bactericidal efficacy of aniline copolymer for 0.5 wt %, and fungicidal efficacy for slightly higher concentration 2 wt %.

Kinetics of Antimicrobial Activity.

Kinetics studies were conducted on 3ABAPANI (ES), which was the most efficient aniline copolymer of the present invention in terms of its speed of killing microorganisms. A suspension of 2% 3ABAPANI (ES) was made in 5 mL of BHI broth, in glass tubes, and sterilized at 121° C. in an autoclave. Thereafter suspensions were inoculated with microorganisms. The initial inoculum of microorganisms was calculated after CFU titration at time zero, and it was $3.4 \times 10^5$ cfu/ml for *Staphylococcus aureus* ATCC 25923, $3.8 \times 10^5$ cfu/ml for *Escherichia coli* ATCC 25922, $3.8 \times 10^5$ cfu/ml for *Pseudomonas aeruginosa* ATCC 27853, and $1.4 \times 10^5$ cfu/ml for *Candida albicans*. Samples of 100 µL were taken at time intervals, ten-fold serially diluted in BHI broth, and from each dilution 100 µL was spread over the entire BHI agar surface plate with a glass rod. After incubation of the BHI agar plates for 48 h at 35° C., the colonies were counted. The minimum detection level was 100 colonies.

Results are expressed as the Log 10 reduction of the growth. Data points marked with an X signify the moment when the viable bacteria could no longer be detected.

The results of the experiments are shown in FIGS. 2 to 5. These show bactericidal as well as fungicidal properties of 3ABAPANI (ES) for 2% concentration. The 3ABAPANI (ES) showed bactericidal effect for 1% but with 4-6 times longer killing time.

Influence of the Inoculum Size on the Antimicrobial Activity of Aniline Copolymers.

The influence of the inoculum size was determined in exactly the same way as the kinetics (the speed of killing or killing rate), with the only difference being the inoculum size. Suspensions containing 2% 3ABAPANI (ES) were made in 5 mL of BHI broth, in glass tubes, and sterilized at 121° C. in an autoclave. Thereafter suspensions were inoculated with microorganisms. The initial inoculum of microorganisms was calculated after CFU titration at time zero, and it was $1.2 \times 10^{10}$ cfu/ml for *Staphylococcus aureus* ATCC 25923. Samples of 100 µL were taken at time intervals, ten-fold serially diluted in BHI broth, and from each dilution 100 µL were spread over the entire BHI agar surface plate with a glass rod. After incubation of the BHI agar plates for 48 h at 35° C., the colonies were counted. The minimum detection level was 100 colonies.

Results are expressed as the Log 10 reduction of the growth, and are shown in FIG. 6. Data points marked with an X represent time when viable bacteria could not be detected. This part of the experiment revealed that inoculum size did not have a significant influence on the antimicrobial activity of copolymers against *Staphylococcus aureus* ATCC 25923. Irrespective of the inoculum size 3ABAPANI (ES) retained its bactericidal effect.

Influence of the Organic Load on the Antimicrobial Activity of Aniline Copolymers.

To determine the influence of organic load on the antimicrobial activity of aniline copolymers, in general the protocol described above for measuring the influence of the inoculum size on the antimicrobial activity of aniline copolymers was used. Suspensions of 3ABAPANI (ES) made in BHI broth, in glass tubes, and sterilized at 121° C. in an autoclave, were mixed with human plasma. The mixture obtained was left for 30 minutes at room temperature. Thereafter the mixture was inoculated with microorganisms. The final volume was 5 mL, and it contained BHI broth, 3ABAPANI (ES) in the final concentration of 2% and human plasma in the final concentration of 20%, 10% or 5%, while the initial inoculum of microorganisms was calculated after CFU titration at time zero, and it was $1.2 \times 10^{10}$ cfu/ml for *Staphylococcus aureus* ATCC 25923, $5.7 \times 10^{11}$ cfu/ml for *Escherichia coli* ATCC 25922, $3.84 \times 10^{11}$ cfu/ml for *Pseudomonas aeruginosa* ATCC 27853, and $8.1 \times 10^7$ cfu/ml *Candida albicans*. Samples of 100 µL were taken at time intervals, ten-fold serially diluted in BHI broth, and from each dilution 100 µL were spread over the entire BHI agar surface plate with a glass rod. After incubation of the BHI agar plates for 48 h at 35° C., the colonies were counted. The minimum detection level was 100 colonies.

Results are expressed as the Log 10 reduction of the growth, and are shown in FIGS. 7 to 11. Data points marked with an X represent time when viable bacteria could not be detected.

This is the worse possible scenario for antimicrobial activity of aniline copolymers: extremely high microbial inoculum, very high (20%) organic load (for this type of experiment 10% is often used, and even less), and finally, plasma instead of serum. These conditions slowed but did not stop the antimicrobial activity of aniline copolymers, against tested bacteria (bactericidal action remains for 20% organic load) and fungi (fungicidal action remains for 5% and fungistatic for 20% organic load).

Influence of the Organic Load on the Antifungal Activity of Aniline Copolymers.

The MBC (minimum bactericidal concentration, and the same for minimum fungicidal concentration-MFC) is defined as the lowest agent concentration yielding no more than 0.1% survival of the initial microorganism inoculum (99.9% killing). Applying this definition to the results of the present invention as illustrated in FIG. 12, then since the initial inoculum was Log 10 8.99, and after 8 h dropped to Log 10 6.32 and after 24 h to Log 10 5.41, 3ABAPANI (ES) in the presence of 10% plasma showed after 24 h fungicidal action (not only fungistatic action).

Influence of N-acetyl-L-cysteine (NAC) on the Antimicrobial Activity of Aniline Copolymers.

The influence of NAC on antimicrobial activity of copolymers was determined for 3ABAPANI (ES) against *Staphylococcus aureus* ATCC 25923.

One (1) mL of 80 mmol NAC was mixed with 2 mL of microorganism to obtain the final concentration (after mixing with polyaniline suspension—see later) of $\sim 10^{10}$ per mL of bacteria (theoretical inoculum). The actual initial inoculum was calculated after CFU titration at time zero. The mixture of NAC+microorganism was left at room temperature for 30 minutes. Then the mixture of NAC+microorganism was mixed with suspensions containing 3ABAPANI (ES) (100 mg) in 2 mL of 2.5 strength BHI broth, in glass tubes (3ABAPANI (ES) (suspension was first sterilized at 121° C. in an autoclave). After all mixing the final volume was 5 mL, and the final concentration of 3ABAPANI (ES) was 2%, with 16 mmol of NAC.

Samples of 100 μL were taken at time intervals, ten-fold serially diluted in 0.9 mL of BHI, and from each dilution 100 μL were spread over the entire BHI agar surface plate with a glass rod. After incubation of the BHI agar plates for 48 h at 35° C., the microorganism colonies were counted. In order to avoid carryover effect, no sample was taken directly from the 3ABAPANI (ES) and BHI mixture, and therefore the minimum detection level was 100 colonies.

NAC significantly increased the antimicrobial activity of 3ABAPANI (ES) as presented in FIG. 13. The system (3ABAPANI+NAC) also shows very strong antioxidant ability.

Antimicrobial Properties of Films—Agar Overlay Method.

Films of Θ4 (polyvinyl alcohol-PVA and 0.7 wt % PANI) coated on polymethyl methacrylate (PMMA) and ρ (PVA and 0.2 wt % Poly3ABA) coated on PMMA were cut into pieces, approximately 1×1 cm. Films were placed at the bottom of a sterile plastic Petri dish, taking care to keep uppermost the film side 5 covered with aniline copolymer or polyaniline.

Thereafter the upper sides of films were covered with 50 μL of *Staphylococcus aureus* ATCC 25923 suspension which contained approximately 103 cfu/mL. The actual number of bacterial cells inoculated onto the surface of the films was determined by 10 plating 50 μL of *Staphylococcus aureus* ATCC 25923 onto the surface of BHI agar. After overnight incubation the number of colonies was counted. It was determined that 367 cells of *Staphylococcus aureus* ATCC 25923 were inoculated onto each film. Bacterial suspensions were placed in the middle of the films and spread over the entire surface of the films with a pipette tip. Thereafter each piece of film was covered with a piece of BHI agar (which was cut from the medium previously poured into separate Petri dishes, and solidified). The plastic Petri dishes, in which the pieces of films were placed, were covered with their lids, and incubated overnight at 35° C. The growth of *Staphylococcus aureus* ATCC 25923 was completely inhibited on the surface of Θ4 (PVA and 0.7 wt % PANT) coated on polymethyl methacrylate (PMMA) and ρ2 (PVA and 0.2 wt % Poly3ABA) coated on PMMA. See FIGS. 14 and 15 as examples. The efficacy of PANI and Poly3ABA was not reduced by incorporating them into PVA coatings.

Since growth was not easy to observe, after 48 h in total of incubation at 35° C. the pieces of BHI agar which covered the pieces of film were carefully removed and a sample was directly taken from the surface of the films with a sterile loop. Samples were inoculated onto BHI agar, and incubated overnight at 35° C. This procedure also enabled determination of whether the growth of bacteria was only inhibited in the presence of polyaniline films, or the bacteria were killed (bacteriostatic vs. bactericidal activity). Bactericidal effects of Θ4 (PVA and PANI) coated on PMMA and μ2 (PVA and Poly3ABA) coated on PMMA against *Staphylococcus aureus* ATCC 25923 were observed. Photographs of the films are shown in FIGS. 14 and 15.)

These results show that the aniline copolymers have antimicrobial activity, with the same MIC as in aniline copolymer powders, in blends or composites with other materials. Examples of materials with which they may be blended or formed into a composite include: polymers including poly(vinyl alcohol), poly(vinyl acetate), poly(methyl methacrylate) and other acrylics, poly(ethylene terephthalate) and other polyesters, polyamides, polyethylene and polypropylene, polyvinylidene fluoride), ethylene vinyl acetate copolymers, methyl acrylate copolymers, butane copolymers, hexane copolymers, rubber, natural rubber latex, acrylic latexes and epoxy latexes, ethyl cellulose, cellulose and other polysaccharides, and proteins, either synthesised by in situ polymerisation or coated on the surface.

Viruses.

Suspensions of the autoclaved polymers 3ABAPANI (ES) and PANI (ES) were prepared in cell culture growth medium (DMEM) at concentrations 2, 1 and 0.4% (w/v). Vaccinia virus (Strain WR) was serially diluted in DMEM to a final concentration between $10^3$-$10^5$ infectious particles per mL. Aliquots of virus were mixed with an equal volume of polymer suspension (and a control volume of DMEM without polymer) 15 and incubated at room temperature with gentle agitation for 1 hour after which an equal volume of each suspension was added directly to duplicate monolayer cultures of CV-1 cells. The inoculum was removed after 1 hour and the cells overlayed with DMEM containing 5% fetal bovine serum. After two days, the medium was removed and the cells stained with 0.5% crystal violet. Infectivity of virus suspensions was determined by counting plaque number and the reduction in infectivity (relative to polymer-free control) determined for each starting concentration of polymer.

Percent of Vaccinia virus that survived after 1 h contact with 3ABAPANI (ES) and PANI (ES) is presented in Table 8. The results are expressed as a percentage of the number of viruses which survived (retained infectivity) after 1 h of contact with the polymers. 3ABAPANI (ES) has resulted in a marked inhibition of viral infectivity, in contrast to PANI (ES). A similar pattern of reduced infectivity was observed with 10× and 100× greater concentrations of viruses for 0.5 wt % and 1 wt % of 3ABAPANI (ES).

TABLE 8

| Concentration (wt %) | 3ABAPANI (ES) | | PANI (ES) | |
|---|---|---|---|---|
| | % of survived virus | Standard Deviation | % of survived virus | Standard Deviation |
| 0.5 | 10.6 | ±1.25 | 107 | ±3.1 |
| 1 | 0.61 | ±0.87 | 100 | ±6.1 |

Although the invention has been described with reference to specific examples, it will be appreciated by those skilled in the art that it may be embodied in many other forms. In particular, features of any one of the various described examples may be provided in any combination in any of the other described examples.

The claims defining the invention are as follows:

1. A method for producing an antimicrobial object comprising:
   i. Synthesizing an aniline copolymer, wherein said copolymer is not polyaniline and is in the more antimicrobialy active Emeraldine Salt (ES) form,
   ii. Incorporating said aniline copolymer as an antimicrobial agent with a nonmetallic non-antimicrobial object through either extrusion, co-extrusion, blow molding, coating, or in situ polymerization.

2. The method according to claim 1, wherein the aniline copolymer is a homopolymer of 3-aminobenzoic acid or a homopolymer of 3-aminosulfonic acid.

3. The method according to claim 1, wherein said aniline copolymer is soluble to at least 0.05 mg/mL in a solvent selected from the group consisting of N-methyl-2-pyrrolidone, pyridine, 2,6-dimethyl pyridine, 2,4,6-trimethyl pyridine, dimethyl sulfoxide, N,N-dimethyl acetamide anhydrous, tetrahydrofuran, diemethylformamide, hexafluoro-2-propanol, chloroform, and dichloromethane.

4. The method of claim 1, wherein said aniline copolymer is selected based on physical color, solubility in water, desired antimicrobial activity, and compatibility with other materials.

5. The method according to claim 1, wherein said aniline copolymer is composed of a single or multiple aniline copolymer species.

6. The method according to claim 1, wherein said aniline copolymer composes 0.1% to 50% of the total object by mass.

7. The method according to claim 1, wherein said object is made of a composite material consisting of at least one aniline copolymer and at least one other non-metallic non-aniline copolymer material.

8. The method according to claim 1, wherein said antimicrobial object is made of a non-polyaniline containing material taken from the list comprising: high density polyethylene, low density polyethylene, polypropyplene, polyurethane, poly(vinyl alcohol), poly(vinyl acetate), poly(methyl methacrylate), acrylic polymers, poly(ethylene terephthalate), poly esters, polyamindes, polyethylene, polyvinylidene fluoride, ethylene vinyl acetate copolymers, methyl acrylate copolymers, butane copolymers, hexane copolymers, rubber, natural rubber latex, acrylic latexes, epoxy latexes, ethyl cellulose, cellulose, polysaccharides, proteins, and composites of such materials.

9. The method according to claim 1, wherein said antimicrobial material is effective against bacteria genera selected from the group consisting of *Bordetella, Neisseria, Legionella, Pseudomonas, Salmonella, Shigella, Erwinia, Enterobacter, Escherichia, Vibrio, Haemophilus, Actinobacillus, Klebsiella, Staphylococcus, Streptococcus, Enterococcus, Corynebacterium, Listeria, Bacillus, Mycobacterium, Enterococcus, Leptospira, Serpulina, Mycoplasma, Bacteroides, Yersinia, Chlamydia, Porphyromonas, Pasteurella, Peptostreptococcus, Propionibacterium, Dermatophilus, Campylobacter, Clostridium* and *Erysipelothrix*.

10. The method according to claim 1, wherein said antimicrobial material is effective against fungal genera selected from the group consisting of *Aspergillus, Blastomyces, Candida, Coccidioides, Cryptococcus, Epidermophyton, Histoplasma, Microsporum, Mucor, Rhizopus, Sporothrix, Trichophyton, Paracoccidioides, Absidia, Fusarium, Penicillium, Torulopsis, Trichosporon, Rhodotorula, Malassezia, Cladosporium, Fonsecea* and *Phialophora*.

11. The method according to claim 1, wherein said copolymer is formed by reaction of aniline with a compound of formula (I):

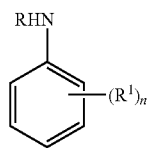

wherein R is hydrogen or a $C_1$-$C_6$ alkyl,
n=1, 2 or 3
$R^1$ is independently selected from the group consisting of:
$C_1$-$C_6$ alkyl,
$C_1$-$C_5$ alkoxyl,
halo,
—$CO_2R^2$
—$SO_3R^2$
—$PO_3HR^2$
—$COR^4$
—$CH_2COOR^4$,
—CN,
—$CH_2OH$,
—$CH_2NH_2$,
—$CH_2CN$,
—OH,
—$SO_2NH_2$;
$R^2$ is selected from hydrogen, $C_1$-$C_5$ alkyl, an alkali metal, ammonium and a substituted ammonium salt;
$R^4$ is selected from hydrogen, $C_1$-$C_6$ alkyl, phenyl; and salts thereof.

12. The method according to claim 11, wherein R is hydrogen, and $R^1$ is —$CO_2R^2$, —$SO_3R^2$, —$OCH_3$, —$CH_3$, or —Cl.

13. The method according to claim 11, wherein the compound of formula I is selected from the group consisting of: 3-aminobenzoic acid, 2-aminobenzoic acid, ethyl 3-aminobenzoate, sulfanilic acid, 2-chloroaniline, o-toluidine and o-anisidine; 3-acetylanfline; 2-aminobenzaldehyde; 2-aminohenzenesfonamide; 2-aminophenol; 3-aminophenol; 2-aminophenylacetic acid; 3-aminophenylacetic acid; 2-aminobenzonitrile; 3-aminobenzonitrile; 2-aminobenzophenone; 3-aminohenzophenone; 2-arninobenzyl alcohol; 3-aminobenzyl alcohol; 2-aminobenzylamine; 2-aminobenzyl cyanide; 2-amino-4-bromobenzoic acid; 2-amino-6-chlorobenzoic acid; 2-amino-4-chlorobenzoic acid; 2-amino-4-chlorophenol; 2-amino-s-rnethylphenol; 2-amino-4,6-dihydroxypyrimidine; 2-amino-1,3-diethylbenzene; 1-amino-3,5-dimethylbenzene; 2-amino-4,6-dimethylpyiidine; 2-amino-4-hydroxy-6-methylpyrimidine; 5-arninoisophthalic acid; 3-amino-2-methylbenzoic add; 2-amino-3-methylphenol; 2-amino-6-methylpyridine; 2-amino-3-picoline; 2-aminopyridine; and 3-aminopyridine.

14. The method according to claim 1, wherein said antimicrobial material is effective against DNA and RNA viruses belonging to families selected from the group consisting of Parvoviridae, Papillomaviridae, Polyomaviridae, Adenoviridae, Hepadnaviridae, Herpesviridae, Poxviridae, Picornaviridae, Caliciviridae, Reoviridae, Togaviridae, Flaviviridae, Coronaviridae, Orthomyxoviridae, Paramyxoviridae, Rhabdoviridae, Filoviridae, Bunyaviridae, Arenaviridae and Retroviridae.

15. The method according to claim 1, wherein said antimicrobial object is employed in the health industry, food industry, packaging industry, water industry, textile industry, plastic industry, glass industry, paper industry, rubber industry, ceramic industry, paint industry, wood industry, poultry industry, seafood industry, sports industry and agricultural industry.

\* \* \* \* \*